United States Patent
Federoff et al.

(10) Patent No.: US 12,076,106 B2
(45) Date of Patent: Sep. 3, 2024

(54) METHOD AND SYSTEM FOR BRAIN ATTACK TRIAGE (BAT)

(71) Applicant: NaviSalute, LLC, Irvine, CA (US)

(72) Inventors: Howard J Federoff, Irvine, CA (US); Ophir Frieder, Chevy Chase, MD (US); Massimo S. Fiandaca, Irvine, CA (US); Ramesh Jain, Irvine, CA (US)

(*) Notice: Subject to any disclaimer, the term of this patent is extended or adjusted under 35 U.S.C. 154(b) by 840 days.

(21) Appl. No.: 17/202,028

(22) Filed: Mar. 15, 2021

(65) Prior Publication Data

US 2021/0298601 A1    Sep. 30, 2021

Related U.S. Application Data

(63) Continuation of application No. 16/111,248, filed on Aug. 24, 2018, now Pat. No. 10,945,604.

(51) Int. Cl.
| | |
|---|---|
| *A61B 5/00* | (2006.01) |
| *A61B 5/374* | (2021.01) |
| *G16H 40/67* | (2018.01) |
| *G16H 50/20* | (2018.01) |
| *G16H 50/30* | (2018.01) |
| *G16H 50/70* | (2018.01) |
| *G16H 80/00* | (2018.01) |

(52) U.S. Cl.
CPC .......... *A61B 5/0022* (2013.01); *A61B 5/7257* (2013.01); *A61B 5/7275* (2013.01); *A61B 5/7282* (2013.01); *A61B 5/0024* (2013.01); *A61B 5/374* (2021.01); *A61B 5/7264* (2013.01); *G16H 80/00* (2018.01)

(58) Field of Classification Search
CPC ... A61B 5/0022; A61B 5/7257; A61B 5/7275; A61B 5/7282; A61B 5/0024; A61B 5/374; A61B 5/7264; G16H 80/00; G16H 40/67; G16H 50/20; G16H 50/30; G16H 50/70
See application file for complete search history.

(56) References Cited

U.S. PATENT DOCUMENTS

2015/0068069 A1*  3/2015  Tran ..................... A43B 13/183
                                                340/693.1

* cited by examiner

*Primary Examiner* — Thaddeus B Cox
*Assistant Examiner* — Joshua Daryl D Lannu

(57) ABSTRACT

Embodiments herein relate to biosensors and other elements combined in real-time for health applications that acquire health data of an individual from one or more data streams by a first element and integrate these data through a second element that is configured to predict and/or recognize an interruptive health event and then via one or more successive elements alert one or more providers of a possible interruptive health event, enable the providers to propose one or more effective interventions, communicate directly with the individual and providers and/or caregivers, and/or provide confirmation in the event that effective interventions were made. Embodiments also relate to predicting and recognizing brain attack in real-time by acquiring and integrating health data from one or more data streams, interfacing with one or more providers so that they can propose and/or effect one or more effective interventions, and communicating with an affected individual, providers, and/or caregivers.

22 Claims, 10 Drawing Sheets

Brain Attack Triage System - Backend Functional Blocks

Referral Scenario - Brain Attack Triage System (BATS)

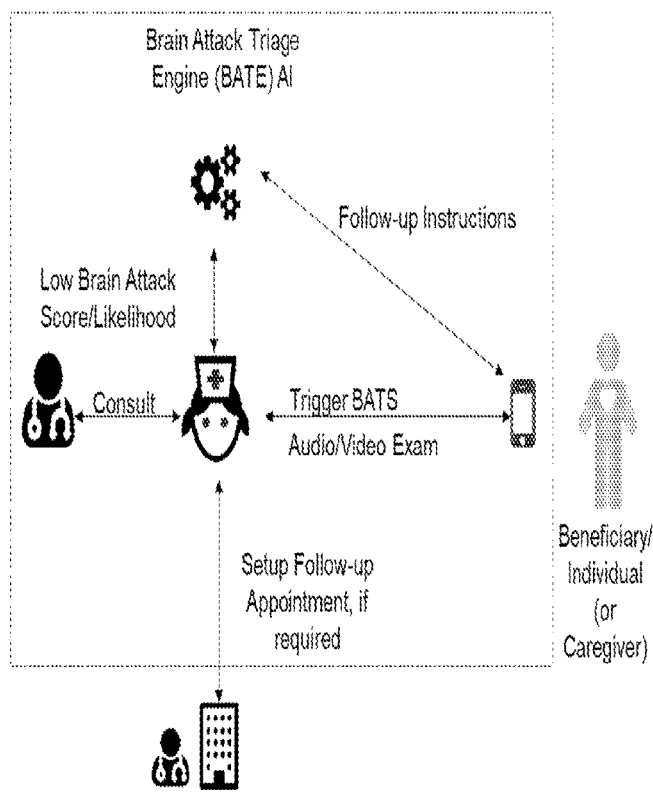

- Remote assessment based on baseline A/V questionnaire, propensity, filter, stratification
- Rapid "live" consultation with RN and on-call MD
- Establish follow-up appointment with PCP/other provider
- Saves overall treatment cost by avoiding hospital referral for false-alarms and by reducing brain attack associated morbidity/mortality

FIG. 2

General –
- Weight loss or gain
- Fatigue
- Fever or chills
- Weakness
- Trouble Sleeping Skin –
- Rashes
- Lumps
- Itching
- Dryness
- Color changes
- Hair and nail changes Head -
- Headache
- Head injury
- Neck Pain Ears –
- Decreased hearing
- Ringing in ears
- Earache
- Drainage Eyes –
- Vision Loss/Changes
- Glasses or contacts
- Pain
- Redness
- Blurry or double vision
- Flashing lights
- Specks
- Glaucoma
- Cataracts
- Last eye exam Nose –
- Stuffiness
- Discharge
- Itching
- Hay fever
- Nosebleeds
- Sinus pain Throat -
- Bleeding
- Dentures
- Sore tongue

- Dry mouth
- Sore throat
- Hoarseness
- Thrush
- Non-healing sores

Neck -
- Lumps
- Swollen glands
- Pain
- Stiffness

Breasts –
- Lumps
- Pain
- Discharge
- Self-exams
- Breast-feeding

Respiratory –
- Cough
- Sputum
- Coughing up blood
- Shortness of breath
- Wheezing
- Painful breathing Cardiovascular –
- Chest pain or discomfort
- Tightness
- Palpitations
- Shortness of breath with activity
- Difficulty breathing lying down
- Swelling
- Sudden awakening from sleep with shortness of breath Gastrointestinal –
- Swallowing difficulties
- Heartburn
- Change in appetite
- Nausea
- Change in bowel habits
- Rectal bleeding
- Constipation
- Diarrhea

- Yellow eyes or skin

Urinary –
- Frequency
- Burning or pain
- Blood in urine
- Incontinence
- Change in urinary strength Vascular –
- Calf pain with walking
- Leg cramping Musculoskeletal –
- Muscle or joint pain
- Stiffness
- Back pain
- Redness of joints
- Swelling of joints
- Trauma Neurologic –
- Dizziness
- Fainting
- Seizures
- Weakness
- Numbness
- Tingling
- Tremor Hematologic –
- Ease of bruising
- Ease of bleeding Endocrine –
- Heat or cold intolerance
- Sweating
- Frequent urination
- Thirst
- Change in appetite Psychiatric –
- Nervousness
- Stress
- Depression
- Memory loss

FIG. 7

| Category | Score/Description | | Date/Time Initials |
|---|---|---|---|
| 1a. Level of Consciousness (Alert, drowsy, etc.) | 0 = Alert<br>1 = Drowsy<br>2 = Stuporous<br>3 = Coma | | |
| 1b. LOC Questions (Month, age) | 0 = Answers both correctly<br>1 = Answers one correctly<br>2 = Incorrect | | |
| 1c. LOC Commands (Open/close eyes, make fist/let go) | 0 = Obeys both correctly<br>1 = Obeys one correctly<br>2 = Incorrect | | |
| 2. Best Gaze (Eyes open – patient follows examiner's finger or face) | 0 = Normal<br>1 = Partial gaze palsy<br>2 = Forced deviation | | |
| 3. Visual Fields (Introduce visual stimulus / threat to pt's visual field quadrants) | 0 = No visual loss<br>1 = Partial Hemianopia<br>2 = Complete Hemianopia<br>3 = Bilateral Hemianopia (Blind) | | |
| 4. Facial Paresis (Show teeth, raise eyebrows and squeeze eyes shut) | 0 = Normal<br>1 = Minor<br>2 = Partial<br>3 = Complete | | |
| 5a. Motor Arm – Left<br>5b. Motor Arm – Right (Elevate arm to 90° if patient is sitting, 45° if supine) | 0 = No drift<br>1 = Drift<br>2 = Can't resist gravity | Left | |
| | 3 = No effort against gravity<br>4 = No movement<br>X = Untestable<br>(Joint fusion or limb amp) | Right | |
| 6a. Motor Leg – Left<br>6b. Motor Leg – Right (Elevate leg 60° with patient supine) | 0 = No drift<br>1 = Drift<br>2 = Can't resist gravity | Left | |
| | 3 = No effort against gravity<br>4 = No movement<br>X = Untestable<br>(Joint fusion or limb amp) | Right | |
| 7. Limb Ataxia (Finger-nose, heel down shin) | 0 = No ataxia<br>1 = Present in one limb<br>2 = Present in two limbs | | |
| 8. Sensory (Pin prick to face, arm, trunk, and leg – compare side to side) | 0 = Normal<br>1 = Partial loss<br>2 = Severe loss | | |
| 9. Best Language (Name item, describe a picture and read sentences) | 0 = No aphasia<br>1 = Mild to moderate aphasia<br>2 = Severe aphasia<br>X = Mute | | |
| 10. Dysarthria (Evaluate speech clarity by patient repeating listed words) | 0 = Normal articulation<br>1 = Mid to moderate slurring of words<br>2 = Near to unintelligible or worse<br>X = Intubated or other physical barrier | | |
| 11. Extinction and Inattention (Use information from prior testing to identify neglect or double simultaneous stimuli testing) | 0 = No neglect<br>1 = Partial neglect<br>2 = Complete neglect | | |
| | TOTAL SCORE | | |

The next two pictures are to be used with Item 9 Best Language:

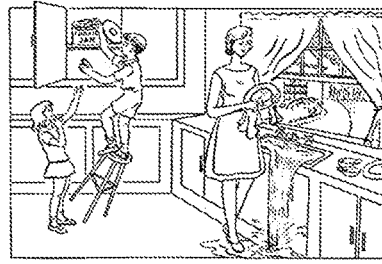

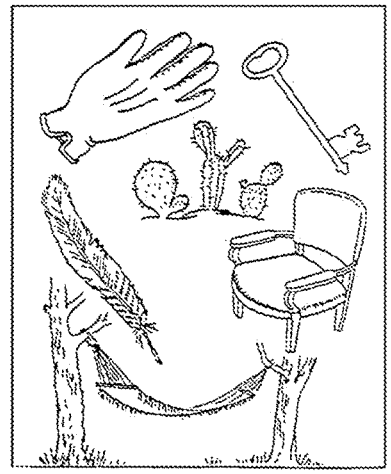

The sentences below are to be read by the patient for Item 9 Best Language:

You know how.
Down to earth.
I got home from work.
Near the table in the dining room.
They heard him speak on the radio last night.

The word list below is to be read by the patient to evaluate for Item 10 Dysarthria:

MAMA
TIP – TOP
FIFTY – FIFTY
THANKS
HUCKLEBERRY
BASEBALL PLAYER

FIG. 8

Table 1. RACE Scale

RACE Scale Score

| Item | Race Score | NIHSS Score Equivalence |
|---|---|---|
| Facial palsy | | |
|   Absent | 0 | 0 |
|   Mild | 1 | 1 |
|   Moderate to severe | 2 | 2-3 |
| Arm motor function | | |
|   Normal to mild | 0 | 0-1 |
|   Moderate | 1 | 2 |
|   Severe | 2 | 3-4 |
| Leg motor function | | |
|   Normal to mild | 0 | 0-1 |
|   Moderate | 1 | 2 |
|   Severe | 2 | 3-4 |
| Head and gaze deviation | | |
|   Absent | 0 | 0 |
|   Present | 1 | 1-2 |
| Aphasia* (if right hemiparesis) | | |
|   Performs both tasks correctly | 0 | 0 |
|   Performs 1 task correctly | 1 | 1 |
|   Performs neither tasks | 2 | 2 |
| Agnosia† (if left hemiparesis) | | |
|   Patient recognizes his/her arm and the impairment | 0 | 0 |
|   Does not recognize his/her arm or the impairment | 1 | 1 |
|   Does not recognize his/her arm nor the impairment | 2 | 2 |
| Score total | 0-9 | |

NIHSS, National Institutes of Health Stroke Scale; and RACE, Rapid Arterial oCclusion Evaluation.
*Aphasia: Ask the patient to (1) "close your eyes"; (2) "make a fist" and evaluate if the patient obeys
†Agnosia: Ask the patient: (1) while showing him/her the paretic arm: "Whose arm is this" and evaluate if the patient recognizes his own arm; (2) "Can you lift both arms and clap" and evaluate if the patient recognizes his functional impairment.

Large Vessel Occlusion Scales Rapid Arterial Occlusion Evaluation (RACE)*
Los Angeles Motor Scale (LAMS)*
Cincinnati Prehospital Stroke Severity Scale (CPSSS)
Field Assessment Stroke Triage for Emergency Destination (FAST-ED)
Prehospital Acute Stroke Severity Scale (PASS)

*Paramedic validation studies – 1) Perez de la Ossa N, Carrera D, Gorchs M, Querol M, Millan M, Gomis M, et al. Design and validation of a prehospital stroke scale to predict large arterial occlusion the rapid arterial occlusion evaluation scale. Stroke. 2014;45:87–91. doi: 10.1161/STROKEAHA.113.003071. 2).
Noorian A, Sanossian N, Liebeskind DS, Starkman S, Eckstein M, Stratton S, et al. Field validation of prehospital lams score to identify large vessel occlusion ischemic stroke patients for direct routing to emergency neuroendovascular centers [abstract]. Stroke. 2016;47:A83.

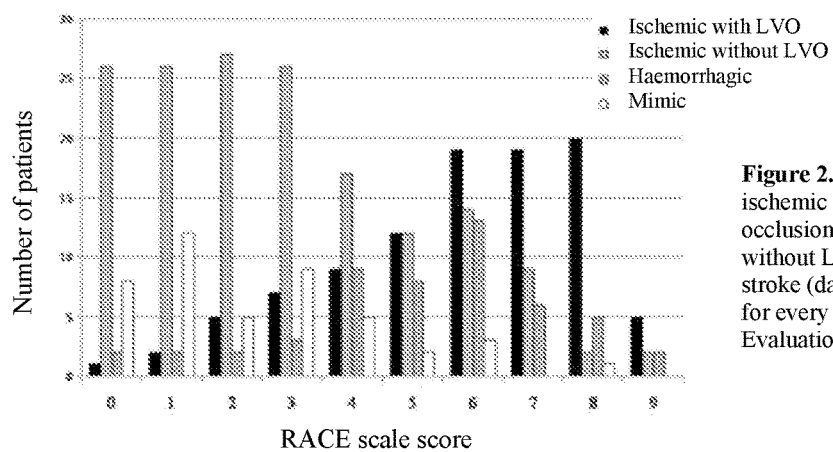

Figure 2. Proportion of patients with ischemic stroke with large vessel occlusion (LVO; black), ischemic stroke without LVO (gray), haemorrhagic stroke (dashed), or stroke mimic (white) for every Rapid Arterial oCclusion Evaluation (RACE) scale score.

FIG. 9

METHOD AND SYSTEM FOR BRAIN ATTACK TRIAGE (BAT)

CROSS-REFERENCE TO RELATED APPLICATIONS

The present application is continuation of U.S. patent application Ser. No. 16/111,248, filed Aug. 24, 2018, (now U.S. Pat. No. 10,945,604 issued Mar. 16, 2021), the disclosure of which is incorporated herein by reference in its entirety as a part of the present application.

BACKGROUND OF INVENTION

An embodiment of the invention relates to tracking interruptive health events and taking actions with respect to such interruptive health events.

Health tracking through biosensors and other elements was demonstrated as a successful technique for tracking health and interruptive health events through monitoring of many different aspects, including physical activity, physiological signs, and blood component levels.

Biosensors and other elements are successfully applied to a wide range of personal health applications including in wearable devices to monitor steps and vital signs and in portable devices to monitor circulatory system molecules. Within this gamut of applications, biosensors and other elements have gained widespread acceptance as high-performance, robust and cost-effective alternatives to expensive medical equipment and interventions at hospitals and other healthcare providers.

Until now, biosensors and other elements have not been used in health applications which acquire health data of an individual from one or more data streams by a first element and integrate these data through a second element that is configured to predict and/or recognize an interruptive health event and then via one or more successive elements alert one or more providers of a possible interruptive health event, enable the providers to propose one or more effective interventions, communicate directly with the individual and providers and/or caregivers, and/or provide confirmation in the event that effective interventions were made. This includes the important health application of predicting and/or recognizing brain attack. People wishing to use biosensors and other elements in this type of application have realized that merely tracking a physiological signal in an individual would not enable the prediction and recognition of interruptive health events in time to propose one or more effective interventions to potentially prevent, mitigate, and/or treat such events. The data acquired from the biosensors and other elements would on their own not have any power to predict or recognize a health deviation that would lead to an interruptive health event, such as a brain attack, before the onset of the health event, and so, would not be effective in remedying the health deviation and in potentially preventing the interruptive health event.

SUMMARY OF INVENTION

An embodiment of the invention makes it possible to use health-tracking systems based on biosensors and other elements by configuring the biosensors and other elements to acquire health data from an individual from one or more data streams, integrating these data to predict and/or recognize interruptive health events, interfacing with one or more providers so that they can propose and/or effect one or more effective interventions, and communicating with an affected individual, providers, and/or caregivers. The advantages of embodiments of the invention apply not only to the prediction and/or recognition of interruptive health events using biosensors and other elements, but also to proposing effective interventions to potentially prevent, mitigate, and/or treat such interruptive health events.

In general, in one aspect, an embodiment of the invention features a system for tracking the health of an individual relative to health norms and deviations relevant to that individual and proposing effective interventions in the event of such deviations. The system includes a first biosensor or set of biosensors configured to acquire a physiological signal from an individual; a first element configured to acquire health data of the individual from one or more data streams; a second element adapted to receive and integrate the physiological signal from the individual and the health data of the individual, wherein the element is configured to predict and/or recognize brain attack in the individual based on an integration of the physiological signal from the individual and the health data of the individual; a third element configured to activate if such identification occurs and alert a first provider via such activation of a possible interruptive health event; and a fourth element configured to interact with the individual in real-time and enable the first provider to propose to the individual and/or a caregiver and/or a second provider one or more effective interventions.

In another aspect, an embodiment of the invention features a system for tracking the health of an individual relative to health norms and deviations relevant to that individual and proposing effective interventions in the event of such deviations. The system includes a first biosensor or set of biosensors configured to acquire a physiological signal from an individual; a first element configured to acquire health data of the individual from one or more data streams; a second element adapted to receive and integrate the physiological signal from the individual and the health data of the individual, wherein the element is configured to predict and/or recognize brain attack in the individual based on an integration of the physiological signal from the individual and the health data of the individual; a third element configured to activate if such identification occurs and alert a first provider via such activation of a possible interruptive health event; a fourth element configured to interact with the individual in real-time and enable the first provider to propose to the individual and/or a caregiver and/or a second provider one or more effective interventions; and a fifth element configured to initiate and interact with the individual and/or first and/or second provider in real-time and determine that effective interventions were made.

A variation of the two embodiments described immediately above may be that the third and fourth element are the same element.

Implementations of an embodiment of the invention may include one or more of the following features. The brain attack tracked may be an ischemic stroke, a hemorrhagic stroke, an intracerebral hemorrhage, a subarachnoid hemorrhage, a seizure, or a secondary ischemic stroke.

Further, implementations of an embodiment of the invention may include one or more of the following features. The biosensor or set of biosensors may include a body-mass-index (BMI) monitor, a physiological stress monitor, a heart monitor, a blood pressure monitor, an oxygen level monitor, a vital signs monitor or combinations thereof. The biosensor or set of biosensors may be worn by the individual.

The first element may be configured to acquire supporting data comprising family health data of family members of the individual, dietary habits data of the individual, behavioral aspects data of the individual or general population norms data. The first element may include a non-biosensor. The non-biosensor may be configured to acquire a non-physiological signal from an accelerometer activity, an acoustic activity, facial recognition, an ambient lighting condition and/or a global positioning system. The biosensor or set of biosensors and the non-biosensor may collect data continuously and unobtrusively. The biosensor or set of biosensors may collect data continuously and unobtrusively and the non-biosensor may collect data periodically or intermittently.

The second element may be configured such that integration of the physiological signal is continuous and real-time. The second element may include an inference engine. The inference engine may integrate the physiological signal from the individual, the health data of the individual and the supporting data to predict and/or recognize brain attack in the individual by assessing impending or newly detected deviations from the individual's normal health trajectories and suggesting to the individual and/or a provider one or more effective interventions to mitigate or prevent significant deviations from the individual's health and toward known disease characteristics.

The third element may comprise an application for a mobile or cellular device that can communicate with the first provider.

The fourth element may comprise an audio or video interface for communication with the individual to conduct an automated brain attack triage procedure. The fourth element may further comprise an audio or video interface for communication with the individual, the first provider, and the second provider to conduct an automated brain attack triage procedure or an augmented brain attack triage procedure mediated by the first provider and/or the second provider.

The fifth element may comprise a text, call, email, audio, or video interface for communication with the individual and/or first provider and/or second provider.

Other embodiments of the invention relate to a system capable of performing a method comprising acquiring a physiological signal from an individual by a biosensor; acquiring health data of the individual from one or more data streams by a first element; integrating the physiological signal from the individual and the health data of the individual using a second element adapted to receive and integrate the physiological signal from the individual and the health data of the individual, wherein the second element is configured to identify a feature associated with brain attack in the individual and activate a third element if such identification occurs; alerting a first provider via activation of the third element of a possible interruptive health event; initiating a fourth element that interacts with the individual in real-time; and proposing via the fourth element to the individual and/or a caregiver and/or a second provider one or more effective interventions.

Other embodiments of the invention relate to a system capable of performing a method comprising: acquiring a physiological signal from an individual by a biosensor; acquiring health data of the individual from one or more data streams by a first element; integrating the physiological signal from the individual and the health data of the individual using a second element adapted to receive and integrate the physiological signal from the individual and the health data of the individual, wherein the second element is configured to identify a feature associated with brain attack in the individual and activate a third element if such identification occurs; alerting a first provider via activation of the third element of a possible interruptive health event, wherein the third element interacts with the individual in real-time; and proposing via the third element to the individual and/or a caregiver and/or a second provider one or more effective interventions.

Yet other embodiments relate to a system for secondary stroke (and other brain attack) prediction and/or recognition, comprising: one or more biosensors configured to acquire a physiological signal from an individual; a first element configured to acquire health data of the individual from one or more data streams; and a second element adapted to receive and integrate the physiological signal from the individual and the health data of the individual, wherein the element is configured to predict and/or recognize secondary ischemic stroke (or other brain attack) in the individual based on an integration of the physiological signal from the individual and the health data of the individual, and to propose to the individual and/or a provider one or more effective interventions.

Yet another embodiment relates to a method, comprising acquiring a physiological signal from an individual by a biosensor; acquiring health data of the individual from one or more data streams by a first element; integrating the physiological signal from the individual and the health data of the individual using a second element adapted to receive and integrate the physiological signal from the individual and the health data of the individual, wherein the second element is configured to identify a feature associated with brain attack in the individual and activate a third element if such identification occurs; alerting a first provider via activation of the third element of a possible interruptive health event; initiating a fourth element that interacts with the individual in real-time; and proposing via the fourth element to the individual and/or a caregiver and/or a second provider one or more effective interventions. Optionally, further fifth element is initiated that interacts with the individual and/or the first and/or second provider in real-time and wherein said fifth element determines that effective interventions were made. Optionally, the brain attack is an ischemic stroke. Optionally, the brain attack is a hemorrhagic stroke. Optionally, the brain attack is an intracerebral hemorrhage. Optionally, the brain attack is a subarachnoid hemorrhage. Optionally, the brain attack is a seizure. Optionally, the brain attack is a secondary ischemic stroke. Optionally, the first element comprises a non-biosensor. Optionally, the first element is further configured to acquire supporting data comprising family health data of family members of the individual, dietary habits data of the individual, behavioral aspects data of the individual or general population norms data. Optionally, the second element comprises an inference engine. Optionally, the inference engine integrates the physiological signal from the individual and the health data of the individual to identify a feature associated with a brain attack in the individual by assessing a deviation from the individual's normal health trajectory indicating a possible interruptive health event and activating a third element if said deviation is detected with the purpose of mitigating or preventing significant deviations from the individual's health and toward known disease characteristics. Optionally, the inference engine integrates the physiological signal(s) from the individual, the health data of the individual, and the supporting data to identify a feature associated with brain attack in the individual by assessing a deviation from the individual's normal health trajectory indicating a possible interruptive health event and activating a third element if said deviation is detected with the purpose of mitigating or preventing significant deviations from the individual's health and toward known disease characteristics. Optionally, the biosensor is a body-mass-index (BMI) monitor, a physiological stress monitor, a heart monitor, a blood pressure monitor, an oxygen level monitor, a vital sign monitor or combinations thereof. Optionally, the biosensor is worn by the individual. Optionally, the non-biosensor is configured to acquire a non-physiological signal from an accelerometer activity, an acoustic activity, an ambient lighting condition and/or a global positioning system. Optionally, the biosensor and the non-biosensor collect data continuously and unobtrusively. Optionally, the biosensor collects data continuously and unobtrusively and the non-biosensor collects data periodically or intermittently. Optionally, the integration of the physiological signal is continuous and real-time. Optionally, the third element comprises an application for a mobile or cellular device that can communicate with the first provider. Optionally, the fourth element comprises an audio or video interface for communication with the individual to conduct an automated brain attack triage procedure. Optionally, the fifth element comprises a text, call, email, audio, or video interference for communication with the individual and/or first provider and/or second provider. Optionally, the fourth element further comprises an audio or video interface for communication with the individual, the first provider, and the second provider to conduct an automated brain attack triage procedure or an augmented brain attack triage procedure mediated by the first provider and/or the second provider. Optionally, the first provider communicates one or more effective interventions based on established brain attack triage procedures to the individual and/or a caregiver and/or the second provider. Optionally, the first provider and the second provider are the same provider. Optionally, the first provider is a nurse or physician and the second provider is an EMS personnel.

Another embodiment relates to a method, comprising acquiring a physiological signal from an individual by a biosensor; acquiring health data of the individual from one or more data streams by a first element; integrating the physiological signal from the individual and the health data of the individual using a second element adapted to receive and integrate the physiological signal from the individual and the health data of the individual, wherein the second element is configured to identify a feature associated with brain attack in the individual and activate a third element if such identification occurs; alerting a first provider via activation of the third element of a possible interruptive health event, wherein the third element interacts with the individual in real-time; and proposing via the third element to the individual and/or a caregiver and/or a second provider one or more effective interventions. Optionally, a further fourth element is initiated that interacts with the individual and/or the first and/or second provider in real-time and wherein said fifth element determines that effective interventions were made Optionally, the brain attack is an ischemic stroke. Optionally, the brain attack is a hemorrhagic stroke. Optionally, the brain attack is an intracerebral hemorrhage. Optionally, the brain attack is a subarachnoid hemorrhage. Optionally, the brain attack is a seizure. Optionally, the brain attack is a secondary ischemic stroke. Optionally, the first element comprises a non-biosensor. Optionally, the first element is further configured to acquire supporting data comprising family health data of family members of the individual, dietary habits data of the individual, behavioral aspects data of the individual or general population norms data. Optionally, second element comprises an inference engine. Optionally, the inference engine integrates the physiological signal from the individual and the health data of the individual to identify a feature associated with a brain attack in the individual by assessing a deviation from the individual's normal health trajectory indicating a possible interruptive health event and activating a third element if said deviation is detected with the purpose of mitigating or preventing significant deviations from the individual's health and toward known disease characteristics. Optionally, the inference engine integrates the physiological signal(s) from the individual, the health data of the individual, and the supporting data to identify a feature associated with brain attack in the individual by assessing a deviation from the individual's normal health trajectory indicating a possible interruptive health event and activating a third element if said deviation is detected with the purpose of mitigating or preventing significant deviations from the individual's health and toward known disease characteristics. Optionally, the biosensor is a body-mass-index (BMI) monitor, a physiological stress monitor, a heart monitor, a blood pressure monitor, an oxygen level monitor, a vital sign monitor or combinations thereof. Optionally, the biosensor is worn by the individual. Optionally, the non-biosensor is configured to acquire a non-physiological signal from an accelerometer activity, an acoustic activity, an ambient lighting condition and/or a global positioning system. Optionally, the biosensor and the non-biosensor collect data continuously and unobtrusively. Optionally, the biosensor collects data continuously and unobtrusively and the non-biosensor collects data periodically or intermittently. Optionally, the integration of the physiological signal is continuous and real-time. Optionally, the third element comprises an application for a mobile or cellular device that can communicate via text messaging and/or via an audio interface and/or via a video interface with the first provider and the individual to conduct an automated brain attack triage procedure and/or an augmented brain attack triage procedure mediated by the first provider. Optionally, the fourth element comprises a text, call, email, audio, or video interference for communication with the individual and/or first provider and/or second provider. Optionally, the third element further comprises an application for a mobile or cellular device that can communicate via text messaging and/or via an audio interface and/or via a video interface with the first provider, the individual, and the second provider to conduct an automated brain attack triage procedure and/or an augmented brain attack triage procedure mediated by the first provider and/or the second provider. Optionally, the first provider communicates one or more effective interventions based on established brain attack triage procedures to the individual and/or a caregiver and/or the second provider. Optionally, the first provider and the second provider are the same provider. Optionally, the first provider is a nurse or physician and the second provider is an EMS personnel.

Other advantages and features will become apparent from the following description and from the claims.

DESCRIPTION OF THE FIGURES

FIG. 2 shows a schematic of BATS scenario 1.

FIG. 7 shows a schematic of a general review of systems checklist.

FIG. 8 shows a schematic of the examination steps that a registering covered subject undergoes for a guided examination.

FIG. 9 shows a schematic for the determination of baseline large vessel occlusion scale score undertaken in accordance with Table 1 and FIG. 2 shown in [Stroke. 2014; 45:87-91].

DETAILED DESCRIPTION

Definition and General Techniques

Figure 1:
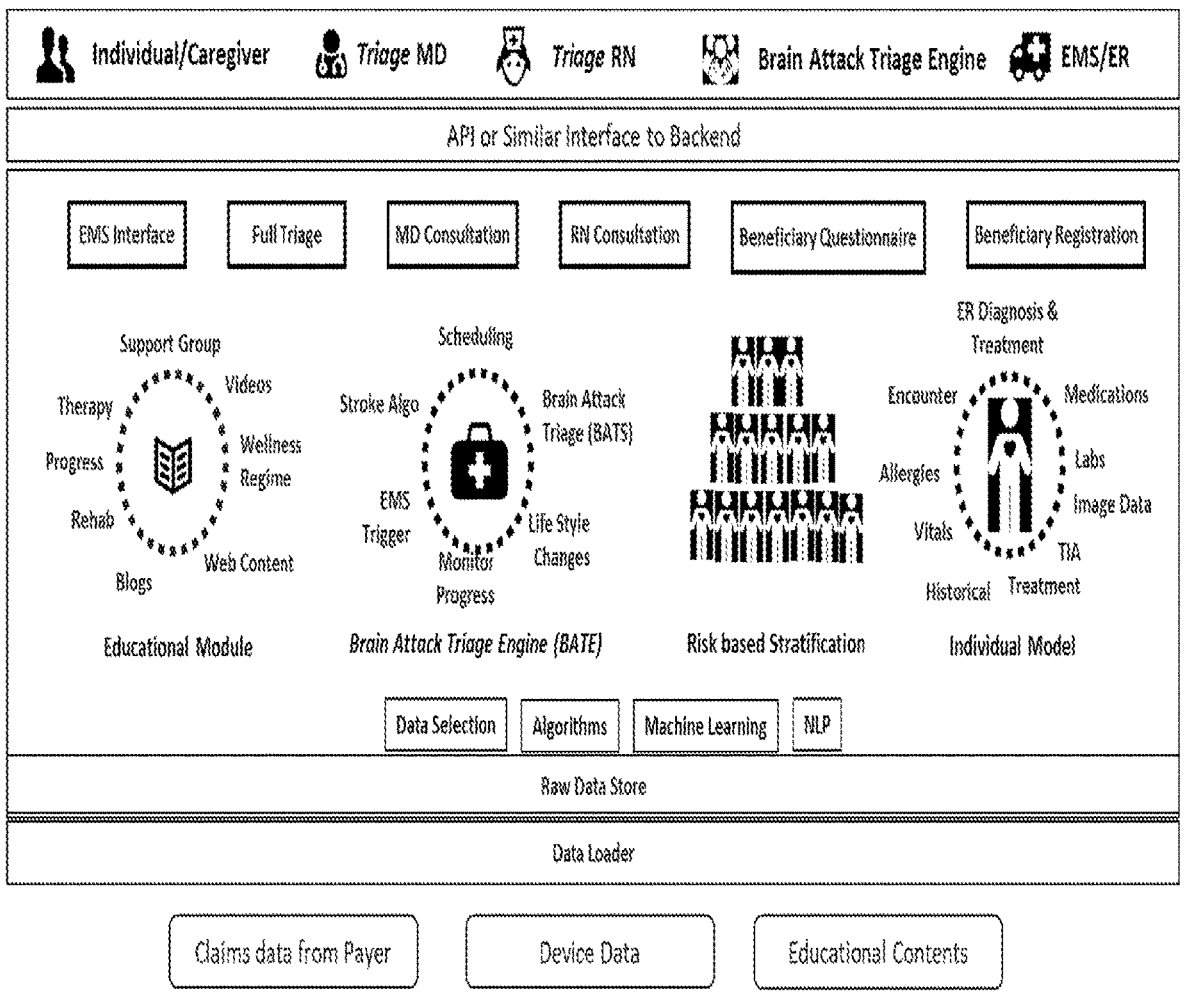
FIG. 1 shows the Brian Attack Triage System (BATS) backend functional blocks.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

The methods and techniques of the present invention are generally performed according to conventional methods well known in the art and as described in various general and more specific references that are cited and discussed throughout the present specification unless otherwise indicated. See, e.g., the American Stroke Association website (http://www.strokeassociation.org/STROKEORG/) and the National Stroke Association website (http://www.stroke.org/), which are incorporated herein by reference. The nomenclatures used in connection with, and the procedures and techniques of, configuring biosensors and other elements described herein are those well-known and commonly used in the art.

The following terms and phrases, unless otherwise indicated, shall be understood to have the following meanings.

The phrase "brain attack" as used herein refers to an emergent neurological event afflicting an individual, of sudden onset and referable to specific brain dysfunction(s). Brain attack includes, but is not limited to, stroke, hemorrhagic stroke, intracerebral hemorrhage, subarachnoid hemorrhage, and seizure. Brain attack, per se, does not imply knowledge as to etiology but only that whatever is afflicting the individual neurologically may require rapid and specific assessment, triage, and treatment for optimal effective intervention and individual outcome.

The term "stroke" as used herein refers to a series of temporal and anatomically localizable neurological dysfunctions that become clinically evident when blood flow is reduced or cut off to a specific brain region, or regions. In this discussion, what is referred to as a stroke is what is known in medicine as an ischemic stroke, and results from lack of blood circulation to the affected region(s) of the brain. The two most common etiologies for ischemic strokes are embolic or thrombotic arterial occlusions. Arteries are the blood vessels originating from the heart that bring oxygenated blood to the body, including the brain. Arteries feed organs like the brain with nourishment and oxygen via capillaries, while waste products and carbon dioxide are taken away from such organs via blood in veins. In embolic arterial occlusion, a particulate aggregate of blood components, usually featuring aggregated platelets, red blood cells, and fibrin, travels from a site of origin (e.g., heart with atrial fibrillation, or arterial vessel with atherosclerotic plaque) to an artery with a smaller lumen and thereby blocks blood flow. In a thrombotic arterial occlusion the local vascular environment is induced to change such that blood and blood flow in an artery cause it to occlude. Common conditions associated with arterial thrombosis include hyperlipidemia, hypercoagulable states, reduced blood flow associated with stenotic arterial diseases, or states with reduced cardiac output. In these conditions, arterial blood has a tendency to form a clot (or thrombus) within the vessel and occlude blood flow beyond such a point. Beyond such a blockage there is a reduction or lack of blood flow and a resultant area of ischemia, or lack of adequate blood supply. In such an ischemic brain region, cells deprived of adequate amounts of oxygen show signs of dysfunction within minutes, and if this hypoxic state is extended, these cells begin to die and result in permanent neurological deficits. Whether the ischemic stroke is embolic or thrombotic, the manifest brain dysfunctions can include altered memory, abnormal balance and coordination, loss of vision or speech, loss of sensation in specific parts of the body, and loss of muscle strength and/or control. In ischemic strokes, clot buster type drugs (e.g., tissue plasminogen activator, TPA) or endovascular embolectomies, if carried out expeditiously, may reduce the loss of brain tissue and degree of permanent neurological impairment.

The phrase "hemorrhagic stroke" as used herein refers to a series of events that are coupled with ischemic stroke but have significant additional consequences to treatments and outcomes. For our purposes, hemorrhagic strokes are considered ischemic strokes where blood supply is somehow re-established following the ischemic insult and results in bleeding into the afflicted brain region due to loss of blood vessel integrity directly related to the ischemic stroke. In cases of hemorrhagic stroke, there is locally increased pressure provided by the blood leaking into the area afflicted by the ischemic stroke, exacerbating neurological deficits. Such individuals would not be candidates for either TPA or embolectomies, since they would exacerbate morbidity and mortality associated with an expanding hemorrhage into the brain. Neurological deficits and outcomes from hemorrhagic strokes are typically worse than from a comparably sized ischemic stroke. The acute diagnosis is typically made between the two types of stroke using computed tomography (CT) scans.

The phrase "intracerebral hemorrhage", or ICH, as used herein will designate an acute rupture and bleeding of an arterial vessel within the brain, most commonly as a result of high blood pressure and specific conditions afflicting brain-specific blood vessels (e.g., arteriolosclerosis, amyloid angiopathy, arteriovenous malformations [AVMs], venous or cavernous angiomas). There are common sites within the brain for ICH to occur that are readily recognizable by neuroradiologists and neurological clinicians. Rather than lack of blood flow causing neurological dysfunction, in these cases the blood bursting into the brain substance causes direct injury to brain cells, while the amount and location of the ICH contributes to the severity of clinical manifestations by either local or diffuse increases in intracranial pressure (ICP). ICP can result in secondary reductions in blood flow with resultant stroke-like consequences as previously discussed. CT scan allows rapid diagnosis of ICH, and TPA and embolectomies are contraindicated. Depending on the size and location of the hemorrhage, medical management versus rapid neurosurgical intervention may be required to reduce morbidity and mortality.

The term "subarachnoid hemorrhage", or SAH, as used herein designates a spontaneous bleeding into the cerebrospinal fluid spaces surrounding the brain. The most common etiologies for SAH are cerebral arterial aneurysms and cerebral AVMs. Both of these conditions have a propensity to present during specific age ranges and classically with individuals complaining of the worst headache of their life. Weakening of blood vessel walls and hemodynamics for both conditions results in the acute bleeding episode. If the bleeding is expressed into the brain as well as the subarachnoid space, an ICH will result, contributing to the clinical manifestations. CT scans typically allow diagnosis to be made, or if negative, may require a lumbar puncture to define evidence of SAH. Magnetic resonance angiography or contrast-based angiography is used to define the abnormal vessel anatomy. Endovascular techniques or open microneurosurgical treatments are required to prevent re-bleeding and for definitive treatment of the etiologic pathology. Morbidity and mortality are associated with the rapid increases in ICP, the ICH (if present), and delayed ischemia resulting from arterial vasospasm (secondary to subarachnoid blood effects). Rapid assessment and treatment, often in intensive care is required for optimal outcomes in these afflicted individuals.

The term "seizure" as used herein is used to indicate an acute neurological dysfunction resulting from uncontrolled intrinsic electrical activity within the brain. Such activity may produce physical convulsions with loss of consciousness, focal numbness or muscle spasms, and altered thinking, among many other features and combinations thereof. Common etiologies include metabolic abnormalities, systemic toxicities, infections, brain tumors, stroke, ICH, SAH, and others. Rapid clinical assessment and diagnostic testing, including an EEG, blood metabolic screen, CT (and/or magnetic resonance imaging) scan, and spinal tap are required for diagnosis. Treatment is usually medical, using anticonvulsant drugs, unless a particular etiology is defined that can be addressed.

The phrase "secondary ischemic stroke" as used herein encompasses the common reoccurrence of an ischemic stroke in individuals with a history of a prior transient ischemic attack or stroke.

The term "biosensor" as used herein refers to an analytical device that is used for the detection of an analyte and that combines a biological component with a physicochemical detector. The biological target, e.g., tissue, microorganism, organelle, cell receptor, enzyme, antibody, or nucleic acid, is a biologically derived material or biomimetic component that interacts, binds, or recognizes with the analyte under study. The transducer or detector transforms one signal into another one and works in a physicochemical way, e.g., optical, piezoelectric, electrochemical, or electrochemiluminescence, to measure and quantify the interaction of the analyte with the biological target.

The phrase "physiological signal" as used herein refers to a quantifiable reading or measurement produced by a physiological process of a human being, e.g., heartbeat, respiratory rate, skin conductance, and/or muscle current.

The term "individual" as used herein refers to a human being.

The term "element" as used herein refers to a tangible device comprising a computing component that can acquire, store, and/or manipulate data from one or more sources. The computing component may be programmable using one or more algorithms.

The phrase "health data" as used herein refers to any quantitative and/or qualitative information relevant to an individual's physical and mental health, encompassing, e.g., individual's vital signs, individual's medical history, weather conditions, and/or workplace conditions.

The term "caregiver" as used herein refers to people who provide care to the individual, including friends, family members, and/or spiritual advisors.

The term "provider" as used herein refers to medical professionals who dispense evidence-based recommendations and provide direct care to the individual, including physicians, nurses, and Emergency Medical Services (EMS) personnel.

The term "triage" as used herein relates to the rapid assessment of an individual by a medical professional and/or a caregiver for the purpose of assigning urgency of care to the subjective or objective complaints raised by the individual and/or their caregivers. Such a triage decision would be informed by knowledge of the individual's medical history, the onset and timing of the individual's complaints or change in status, the alterations in sensor data from baseline, the alterations in baseline neurological assessments and scores, alterations in video and audio data from baseline, and the acute clinical impression of the designated triage caregiver.

The phrase "effective intervention" as used herein refers to the assessment, triage, and if necessary, the specified treatment of an individual following a relevant clinical complaint that results in a change in behavior or medical status of said individual that approaches a return to a baseline health status or trajectory.

The term "non-biosensor" as used herein refers to a device that is configured to acquire a non-physiological signal from, e.g., an accelerometer activity, an acoustic activity, an ambient lighting condition, and/or a global positioning system.

The phrase "supporting data" as used herein refers to any quantitative and/or qualitative information relevant to an individual's physical and mental health, encompassing, e.g., family health data of family members of the individual, dietary habits data of the individual, behavioral aspects data of the individual, and/or general population norms data.

The phrase "inference engine" as used herein refers to a tangible component of a system that applies logical rules to a database of existing information to deduce new information (i.e., brain attack triage engine, or BATE).

The phrase "normal health trajectory" as used herein refers to the progression of an individual's health under conditions of proper exercise, dietary, behavioral, medical and other regimens, so as to diminish and/or prevent the occurrence of interruptive health events.

The phrase "interruptive health event" as used herein refers to the occurrence of a physiological event in an individual that results in death or that necessitates medical intervention or treatment to prevent permanent injury or death.

The disclosed invention changes healthcare orientation by directing attention to individuals and their respective personalized norms and not population health standards defined epidemiologically. Effectively, an embodiment of the invention builds populations by adding individuals, one person at a time, noting that variations will occur even when singular subjects may apparently belong to the same epidemiologic group. The evolutionary entropy (directionality) provided by an individual, therefore, is critical to each person's ability to optimize their health status, and thereby the health of the entire population.

The disclosed invention capitalizes on progress in multi-omic measures, biosensors, computing systems, and mobile technology towards a healthy existence by altering the way we approach health and wellness. Using custom or/and off-the-shelf biosensor technology, an embodiment of the invention gathers manageable data; converts these data to information and creates knowledge-guided systems. This biosensor-based data to knowledge pipeline is fostering a health revolution via three continuously operating steps: health data acquisition via biosensors and other elements, health data processing via an element such as an inference engine to convert the data to knowledge, and then, via an inference engine, proposing effective intervention to sustain a health and wellness for the individual user, and in the aggregate a population.

The health enhancement architecture consists of data capturing elements and devices, such as wearable and other types of biosensors and non-biosensors potentially coupled to smartphones that transmit the collected data for further processing to a second element, such as an, as known in the art, inference engine. The latter executes its function on the computing platform, by ingesting data and learning from an individual's normative values correlated to a health and wellness target, otherwise known as the directly observable health-related characteristics of an individual. Through time-dependent iterative learning, the inference engine monitors an individual's gathered data points for deviations from the personalized established norms, and if necessary, prescribes interventions to maintain the individual's health trajectory. This is critical because the United States public health task force data do not apply to every individual (for example, without limitation, see the controversy regarding mammography or PSA use). Therefore, the established individual's norms are key. Moreover, sharing ownership between providers and patients ensures better alignment and likely better compliance. Naturally not every patient will of course be different.

As a person's telemetry monitoring is continuously gathered (24/7) by biosensors and other elements, during real-life conditions, the inference engine can continuously monitor the success of the prescribed intervention(s). If the prescribed remedies are unsuccessful, alternative solutions are prescribed. The individual user and their predetermined healthcare response teams (providers) are notified of the prescribed interventions and their apparent effects. The aforementioned providers include but are not limited to friends, family members, medical or other caregivers, spiritual advisors, etc. Similarly, these interventions are logged for possible future considerations, can be integrated into the individual's electronic health records and are amenable for additional analyses.

An embodiment of the invention requires a continuous stream of input data acquired through biosensors and other elements. That is, a pipeline is required that consists of data collection, correction, manipulation, storage, processing, and integration of a diverse set of components. Without loss of generality, these data artifacts are captured by sensors that include electronic signals, sound waves, imaging, text patterns (both spoken and written), facial gestures, electronic records, analytic variable values, etc. It is likewise within the scope of an embodiment of the invention that only some of these signals are included in an embodiment.

Data collection and integration are accomplished using any of the known elements and techniques in the art. One such example of data collection and integration is via the use of a "personicle." A personicle, or personal chronicle, passively collects personal data signals and automatically converts them into a log of daily activities via an inference engine, as is known in the art. That is, activities are a composition of meaningful events, which themselves, are derived from the integration and mining of various biosensor readings and time-dependent data values. Open source solutions are known in the art that support such processing. A plurality of biosensors and other elements and information sources are integrated; without loss of generality, the desired data are captured using mobile phones, wearable sensors, and other sensing devices.

Likewise, data granularity issues are addressed. Specifically, as data are collected using biosensors and other elements at different periodicity, their granularity differs. That is, some data are able to be collected continuously, while other data points are collected only hourly, daily, or at longer time intervals. More so, some data are collected on a regular schedule, while others are collected on an "as needed" basis. Finally, some data readings are quantitative and specific, while others are merely qualitative, e.g., "within the defined normal range". Such data integration is accomplished either via a personicle or using other techniques known in the art.

In one embodiment, in processing the data using an element such as an inference engine, security and ethical constraints are acknowledged and rectified. Using cryptographic and privacy approaches known in the art, data security and personal privacy are maintained. Standards known in the art related to ethical concerns about the use of the data, and how to balance the global good for the population, or the individual, versus the privacy concerns of the individual are followed.

In addition to individual patient data, population related data are developed using a "bottom-up" methodology, utilizing multiple individual data sets integrated to provide improved understanding of a population, allowing for the identification of parameters that define the range of individual norms and deviations from such norms. That is, data related to illnesses, medications, behaviors, etc. for a population as a whole are integrated via combining data points from individuals, assessed by the inference engine to guide specific corrective measures. The population may be classified and weighted according to the degree of relevancy provided by a particular individual, and vice versa; for example, characteristics such as, without loss of generality, age group, ethnicity, cultural, locus of domicile or socio-economic background, past medical history, etc. can be used to weigh the characterization of the population or of a particular individual within the population. Similarly, environmental data are likewise integrated with appropriate bias in weighting to reflect effects on the individual and via integration of multiple individual data sets, inferring population effects.

FIG. 1 illustrates the backend functional blocks of a Brain Attack Triage System (BATS). As shown, there are differing representations and control options available depending on the role of the user within the BATS; that is, differing options exist for the individual/caregiver, the triage MD and RN, the EMS/ER provider, and the user monitoring the activities of Brain Attack Triage Engine (BATE). Selection options for the input sources, e.g., claims data from payer, device data, and education contents, likewise exist. Monitors and controls for the Educational, BATE, Risk Based Stratification, and Individual Modules are similarly presented. It is however within the scope of this invention that some of the illustrated modules are combined, some are missing, and some are added as needed to support the BATS functionality disclosed herein.

FIGS. 2 to 6 describe three BATS scenarios.

Figure 3:
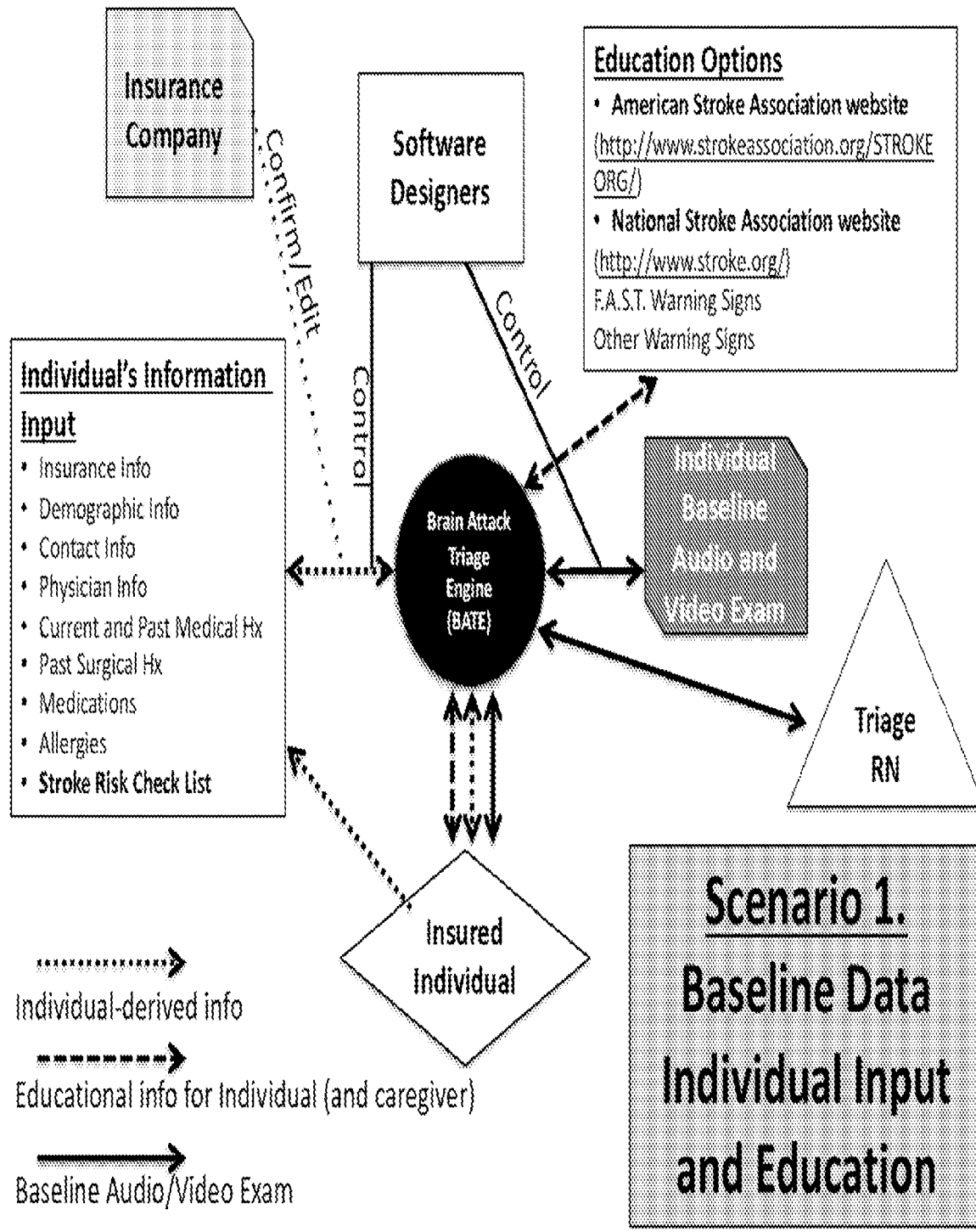
FIG. 3 shows a schematic of BATS scenario 1.

FIGS. 2 and 3 illustrate BATS Scenario 1: Baseline Data, Individual Input, and Education. Introduction of the BATS includes input required for the insured Individual's information, provided by the individual, caregiver and insurance company, inclusive of as much medical history as possible, especially relevant to risk of brain attacks. Baseline Audio/Video exam is carried out on the insured individual according to typical Brain Attack Assessments. The Individual (and their caregivers) utilize the Education Sources incorporated within the BATS for basic and more advanced educational information regarding brain attacks, utilizing research and interactive educational modules and functions provided. The more informed the individual and their caregivers are regarding brain attack identification, and what to do in those instances, the less likely there is to be a misdiagnosis or a delay in treatment.

Figure 4:
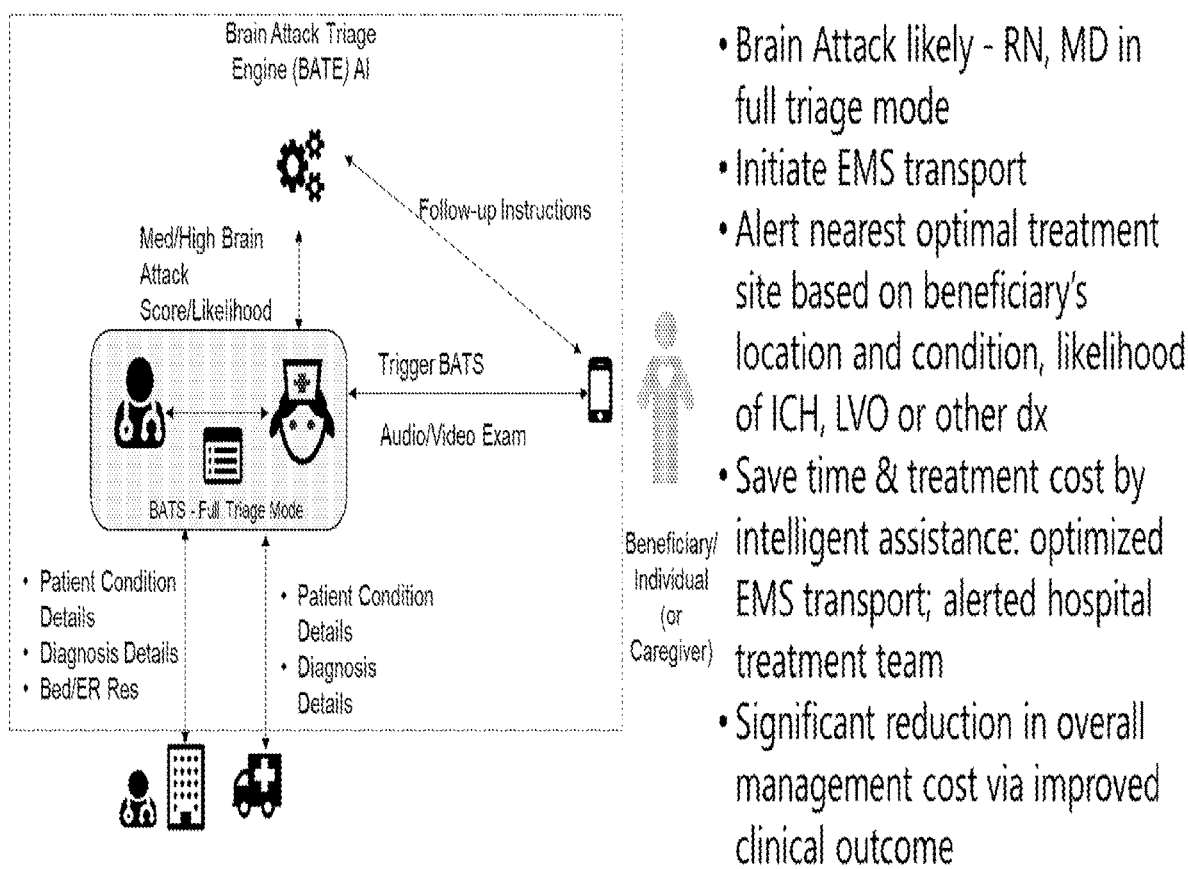
FIG. 4 shows a schematic of BATS scenario 2.
Figure 5:
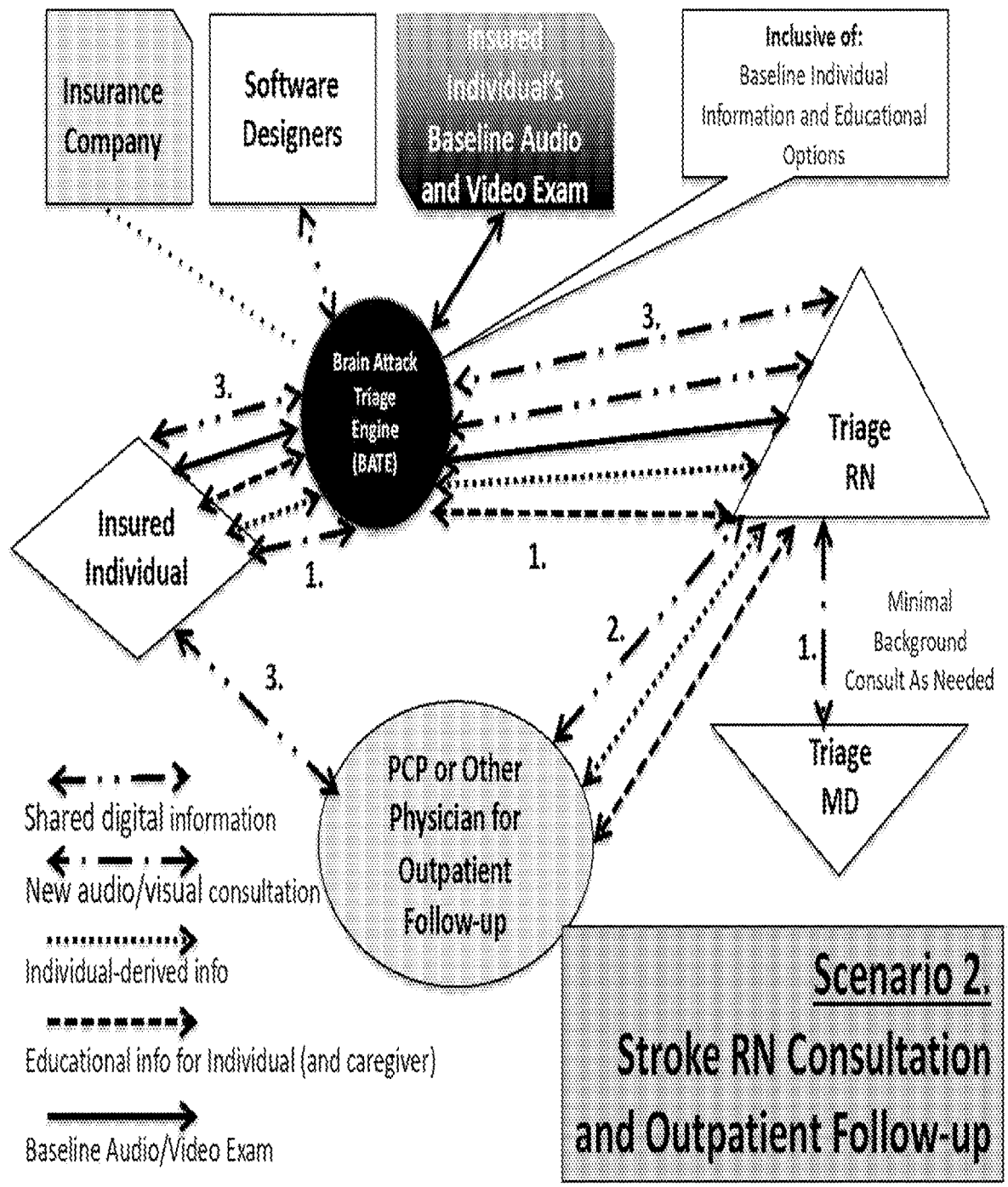
FIG. 5 shows a schematic of BATS scenario 2.

FIGS. 4 and 5 illustrate BATS Scenario 2: Brain Attack RN Consultation and Outpatient Follow-up. (1) Based on a perceived problem, the individual (or caregiver) activate the BATS, or the Brain Attack Triage Engine (BATE) activates communication and assessment based on perceived abnormalities provided via sensors, compared to baseline values. The On-Call Brain Attack Triage RN is alerted and rapidly reviews client's past clinical information via the BATE, while the individual is being assessed and recorded by the AI-driven BATE Audio/Video Q/A session. Based on answers provided to AI questions, the Triage RN gets immediately involved or has additional time to review the individual's baseline audio and video exams prior to direct interaction. Following the scripted AI Q&A session, the RN directly evaluates the individual via a new video/audio interview/exam. If a Brain Attack is not likely (RN may consult on-call physician, if necessary), the Triage RN will discuss relevant clinical issues with individual and/or caregiver(s) and define a follow-up plan, including (2) communication with PCP and/or other providers' answering service or office, sharing information and scheduling outpatient appointment for the individual to make sure specific issues are definitively addressed. Timing of follow-up assessment will be based on best clinical judgment. (3) All relevant information regarding the BATS activation is shared with individual (and caregiver) via BATE and via direct communication via Triage RN with individual. Relevant information is also shared between the Triage RN and the referral office office, that latter which will reconfirm with the individual (and caregiver).

Figure 6:
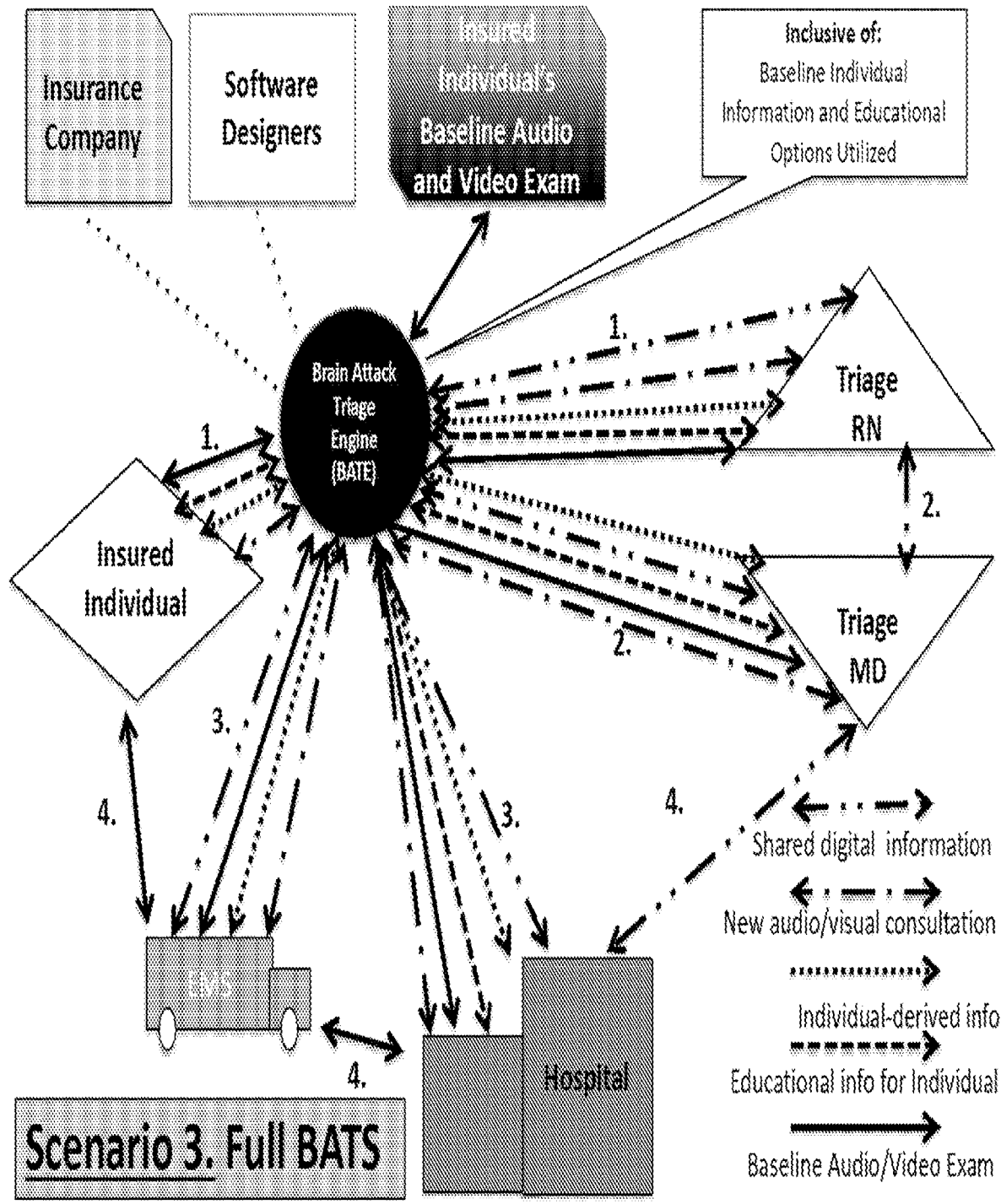
FIG. 6 shows a schematic of BATS scenario 3.

FIG. 6 illustrates BATS Scenario 3. Full BATS. (1) Based on a perceived problem, the individual (or caregiver) activate the BATS, or the BATE activates communication and assessment based on assessed abnormalities provided via sensors, compared to baseline values. The On-Call Brain Attack Triage RN is alerted and rapidly reviews client's past clinical information via the BATE, while the individual is being assessed and recorded by the AI-driven BATE Audio/Video Q/A session. Based on answers provided to AI questions, the Triage RN gets immediately involved or has additional time to review the individual's baseline audio and video exams prior to direct interaction. Following AI Q&A session, nurse directly assesses problem via video/audio interview/examination. (2) When a brain attack is thought to be likely, the RN involves the Triage MD, who along with the Triage RN perform a rapid assessment of the available information, including AI Q&A results, and video/audio interview/exams, in comparison with baseline. (3) Confirmation of likely brain attack by MD triggers communication with EMS for transport, as well as alerting of preferred hospital for treatment via the BATE. Digital information is shared with EMS and hospital. (4) Supplementary communication initiated between Individual (or caregiver)-EMS-Hospital-and Triage RN/MD providers, until individual's transport is completed and arrival to hospital for definitive assessment and treatment. Additional digital alerts sent to individual's other healthcare providers, with summary of assessments, triage decision, and location of treatment site.

The BATS is a patient-centered triaging approach in response to acute cerebrovascular events.

A. The F.A.S.T. warning signs, as summarized below, are well established in the art:
  1. Face drooping. Is one side of the face drooping or numb? The person is asked to smile or show their teeth. Does smile or view of the teeth appear uneven or asymmetrical?
  2. Arm weakness. Does the person report that one arm is weak or numb? Ask them to raise both arms out in front of them. Is one arm unable to be lifted drifts down with gravity?
  3. Speech difficulty. Does the person slur their speech? Can the person easily speak or is what they are saying difficult to understand? Ask the person to repeat a simple sentence, like "The quick brown fox." Is the person able to correctly repeat the words?
  4. Time to call 911 (or activate BATS). If someone you know has any of these signs, even if they go away, call 9-1-1 and say, "I think I am witnessing a brain attack. The person I am with needs transport to the hospital immediately." Time is of the essence! Rapid intervention can save brain cells and lives! Note the time when the noted problems first appeared since emergency responders will need this information.

B. Other important warning signs of brain attack include:
  1. Sudden difficulty understanding speech
  2. Sudden loss of consciousness or confusion
  3. Sudden loss of vision, in one or both eyes
  4. Sudden difficulty walking, loss of balance, or loss of coordination
  5. Sudden severe headache C. The BATS Application Baseline Assessment comprises the following:
  1. Input Medical Information @ BATS Registration includes the following:
    a. Covered Subject Name (Last, First, MI)
    b. Covered Subject Home Address
    c. Covered Subject Home Phone #
    d. Covered Subject Cell Phone #
    e. Covered Subject Work Phone #
    f. Covered Subject Home email address
    g. Covered Subject Work email address
    h. Covered Subject Work Address
    i. Name of Covered Subject Employer
    j. Covered Subject Job Title
    k. Covered Subject Insurance Plan
    l. Covered Subject Insurance Plan #
    m. Name of Primary Insured Individual, if other than Covered Subject
    n. Covered Subject Birth Date (MMDDYYYY)
    o. Covered Subject Sex
    p. Covered Subject Last registered weight (lbs. or kg, MMDDYYYY)
    q. Covered Subject Last registered height (in or cm, MMDDYYYY)
    r. Covered Subject's Primary Care Physician a. (Name, degree)
   b. (Office Address)
   c. (Office Phone #)
   d. (Cell Phone #)
   e. (Email address)
   f. (Primary hospital affiliations)
   s. Covered Subject's Specialist Physician(s)
      i. (Name, degree, Specialty)
      ii. (Name, degree)
      iii. (Office Address)
      iv. (Office Phone #)
      v. (Cell Phone #)
      vi. (Email address)
      vii. (Primary hospital affiliations)
2. Allergies (Y/N), list if present
3. Medications (Y/N)
   a. Prescribed Drug(s) (name, daily dosage)
   b. Non-prescribed Drug(s) (name, daily dosage)
   c. Vitamins (name, daily dosage)
   d. Supplements (name, daily dosage)
4. Past Medical History
   a. General Review of Systems Checklist as shown in FIG. 7.
   b. Stroke Risk Checklist
      i. High Blood Pressure (Y/N)
      ii. Diabetes mellitus (Y/N)
      iii. Cerebrovascular disease (Y/N)
      iv. Past stroke or mini-stroke (Y/N)
      v. Past heart attack (Y/N)
      vi. Atrial Fibrillation (Y/N)
      vii. Patent Foramen Ovale (Y/N)
      viii. Deep Vein Thrombosis or Pulmonary Embolism (Y/N)
      ix. Kidney Disease (Y/N)
      x. Liver Disease (Y/N)
      xi. Blood Clotting Problems (Y/N)
   c. Details of Active Illness
      i. Name of Illness
      ii. Date Diagnosed (MMDDYYYY)
      iii. Specific Treating Physician
5. Past Surgical History
   a. Procedure
i. date (MMDDYYYY)
ii. Surgeon name(s)
iii. City, State
iv. Hospital
v. Results/Complications
6. Recent Laboratory Studies
   a. Lab Test(s)
      i. Date of test
      ii. Results
7. Recent Radiographic Studies
   b. Study Name(s)
      i. Date of study
      ii. Results D. Baseline Video/Audio @ BATS Registration The Registering Covered Subject undergoes a guided examination (in accordance with the examination steps shown in FIG. 8), captured on video and audio, using two commonly used measures of assessment for individuals suffering from a possible stroke. This baseline information is updated yearly and utilized for comparison should an emergent event occur that triggers the BATS.

1. National Institutes of Health Stroke Scale (NIHSS)
   a. NIHSS—"FLEAS Give me a Stroke" pneumonic.
      i. F=Face
      ii. L=Level of consciousness (LOC)
      iii. E=Eyes
      iv. A=Arms/Legs
      v. S=Speech
2. Determination of Baseline Large Vessel Occlusion Scale Score is undertaken in accordance with Table 1 and FIG. 2 shown in Stroke. 2014; 45:87-91 (which are shown in FIG. 9).

The results of the RACE (Rapid Arterial oCclusion Evaluation) scores (obtained from *Stroke*. 2017; 48:00-00) are shown below in Tables 1-3 below:

TABLE 1

Overall Agreement of LVO Scales With CT Imaging

| Scale | Accuracy | Kappa (95% CI) | Sens | Spec | PPV | NPV | AUC | DOR |
|---|---|---|---|---|---|---|---|---|
| RACE ≥ 5 | 0.86 | 0.51 (0.41-0.60) | 0.66 | 0.90 | 0.48 | 0.93 | 0.78 | 17.50 |
| LAMS ≥ 4 | 0.83 | 0.43 (0.34-0.52) | 0.66 | 0.86 | 0.48 | 0.93 | 0.76 | 11.80 |
| FAST-ED ≥ 4 | 0.85 | 0.49 (0.40-0.58) | 0.70 | 0.88 | 0.48 | 0.92 | 0.79 | 26.40 |
| PASS ≥ 2 | 0.81 | 0.43 (0.34-0.52) | 0.71 | 0.84 | 0.45 | 0.93 | 0.77 | 12.40 |
| CPSSS ≥ 2 | 0.81 | 0.35 (0.26-0.45) | 0.56 | 0.86 | 0.42 | 0.91 | 0.71 | 7.54 |

Prevalence = 14.5%. AUC indicates area under receiver-operator curve value; CI, confidence interval; CPSSS, Cincinnati Prehospital Stroke Severity Scale; CT, computed tomography; DOR, diagnostic odds ratio; FAST-ED, Field Assessment Stroke Triage for Emergency Destination; LAMS, Los Angeles Motor Scale; LVO, large vessel occlusion: NPV, negative predictive value; PASS, Prehospital Acute Stroke Severity scale; PN positive predictive value; RACE, Rapid Arterial Occlusion Evaluation; Sens, sensitivity; and Spec, specificity.

TABLE 2

Site of Occlusion/Abnormality for Typical and Atypical Groups

| | Typical | Proportion, % | Atypical | Proportion, |
|---|---|---|---|---|
| LVO* | | | | |
| Extracranial ICA | 3/3 | 5.9 | 2/1 | 6.5/3.2 |
| Intracranial ICA | 5/5 | 9.8 | 1/1 | 3.2/3.2 |
| Tandem occlusion | 1/1 | 2.0 | 1/0 | 3.2/0 |
| M1 MCA | 35/35 | 68.6 | 5/2 | 16.1/6.5 |
| M2 proximal MCA | 6/6 | 11.7 | 18/11 | 58.1/35.5 |
| Dissection | 1/1 | 2.0 | 0 | 0 |
| ICAD | 0 | 0 | 3/1 | 9.7/3.2 |
| Stent occlusion ICA | 0 | 0 | 1/1 | 3.2/3.2 |
| Total | 51 | 100 | 31 | 100 |
| Non-LVO | | | | |
| M2 distal MCA | 9 | 2.1 | 0 | 0 |
| M3/M4 MCA or ACA | 71 | 16.4 | 5 | 10.0 |
| Subcortical | 25 | 5.8 | 4 | 8.0 |
| Basilar | 1 | 0.2 | 2 | 4.0 |
| Other posterior† | 28 | 6.5 | 0 | 0 |

TABLE 2-continued

Site of Occlusion/Abnormality for Typical and Atypical Groups

|  | Typical | Proportion, % | Atypical | Proportion, % |
|---|---|---|---|---|
| Stroke NI† | 30 | 6.9 | 0 | 0 |
| TIA† | 49 | 11.3 | 0 | 0 |
| ICH† | 27 | 6.2 | 32 | 64.0 |
| Stroke mimics† | 193 | 44.6 | 7 | 14.0 |
| Total | 433 | 100 | 50 | 100 |

ICA indicates internal carotid artery;
ICAD, intracranial atherosclerotic disease;
ICH, intracerebral hemorrhage;
LVO, large vessel occlusion;
MCA, middle cerebral artery;
NIHSS, National Institutes of Health Stroke Scale;
Stroke NI, stroke diagnosis with no abnormality on imaging; and
TIA, transient ischemic attack.
*Reported as total number/number with NIHSS ≥ 6.
†Includes infarcts in vertebral, superior/inferior cerebellar, and posterior cerebral arterial territories.

TABLE 3

Proportion of Agreement Between LVO Scales and CT Imaging for Typical and Atypical Groups

|  | Typical | | Atypical | |
|---|---|---|---|---|
| Scale | LVO (95% CI) | Non-LVO (95% CI) | LVO (95% CI) | Non-LVO (95% CI) |
| RACE ≥5 | 0.96 (0.91-1.0) | 0.97 (0.95-0.99) | 0.16 (0.02-0.30) | 0.30 (0.17-0.43) |
| LAMS ≥4 | 0.94 (0.87-1.0) | 0.95 (0.93-0.97) | 0.19 (0.05-0.34) | 0.08 (0.0-0.16) |
| FAST-ED ≥4 | 0.98 (0.94-1.0) | 0.97 (0.96-0.99) | 0.23 (0.07-0.38) | 0.04 (0.0-0.10) |
| PASS ≥2 | 0.96 (0.91-1.0) | 0.92 (0.90-0.95) | 0.29 (0.12-0.46) | 0.06 (0.0-0.13) |
| CPSSS ≥2 | 0.88 (0.79-0.97) | 0.94 (0.92-0.96) | 0.03 (0-0.10) | 0.10 (0.01-0.19) |

CI indicates confidence interval;
CPSSS, Cincinnati Prehospital Stroke Severity Scale;
CT, computed tomography;
FAST-ED, Field Assessment Stroke Triage for Emergency Destination;
LAMS, Los Angeles Motor Scale;
LVO, large vessel occlusion;
PASS, Prehospital Acute Stroke Severity scale; and
RACE, Rapid Arterial Occlusion Evaluation.

3. BATS Activation (Example for John Q. Public)
   a. Activation of the mobile app BATS Alert function results in a text alert sent to the "on call Brain Attack Triage Nurse" that a potential assessment will be required in the near term, providing encrypted link to the covered subject's baseline information for the nurse's rapid review.
   b. Activation of the BATS function activates the microphone and videoconference camera function of the dedicated cell phone and initiates an artificial intelligence (AI)-driven set of questions and answers from within the BATE that initiates communication with the individual and/or caregiver regarding the activating event. It is possible that the BATE will activate the system itself, if input sensor readings deviate significantly from baseline readings. BATE self-activation of AI communication is coupled to alerting of Triage RN to monitor condition and get involved, as needed. BATE will attempt to alert individual, and caregiver if at all possible. If unable to communicate directly, will localize individual via global positioning sensors and alert EMS, if agreed by Triage RN.
   c. The AI driven communication paradigm will feature a discourse similar to the following:

Initial Greeting. "Hello. the Brain Attack Triage System for Mr. Public has been activated. With whom am I communicating?"
<Insured Individual—John Q. Public>
<Mr. Public's Caregiver(s)>
(Video and audio of the individual providing the initial information is obtained and stored for future reference)
   E. Rapid Assessment of Brain Attack Likelihood, using modified F.A.S.T. questions.
      1. "Is Mr. Public awake and alert?" (Y/N)
         "Your answer was Yes, correct?" (Y/N). (If answer to secondary question is Yes, go to next question. If answer to secondary question is No, repeat initial question.)
      2. "Is Mr. Public experiencing Sudden Severe Headache?" (Y/N)
         "Your answer was Yes, correct?" (Y/N). (If answer to secondary question is Yes, go to next question. If answer to secondary question is No, repeat initial question.)
      3. "Is Mr. Public experiencing Sudden Weakness of One Arm?" (Y/N)
         "Your answer was Yes, correct?" (Y/N). (If answer to secondary question is Yes, go to next question. If answer to secondary question is No, repeat initial question.)
      4. "Is Mr. Public experiencing Sudden Loss of Vision In One Eye?" (Y/N)
         "Your answer was Yes, correct?" (Y/N). (If answer to secondary question is Yes, go to next question. If answer to secondary question is No, repeat initial question.)
      5. "Is Mr. Public experiencing Sudden Weakness On One Side of the Face?" (Y/N)
         "Your answer was Yes, correct?" (Y/N). (If answer to secondary question is Yes, go to next question. If answer to secondary question is No, repeat initial question.)
      6. "Is Mr. Public experiencing Sudden Problems Speaking?" (Y/N)
         "Your answer was Yes, correct?" (Y/N). (If answer to secondary question is Yes, go to next question. If answer to secondary question is No, repeat initial question.)

F. Brain Attack Triage Nurse Assessment
   If the answer to questions 1 or 2 is "No", the Triage RN is immediately connected and able to rapidly advance through the assessment. If both answers are "Yes", the Triage RN may observe and listen to the answers provided to questions 3-6. The BATE will collect and provide a digital summary of the Q&A to the RN.
   Using the activated audio and video function of the BATS, and with the assistance of the individual (or caregiver) the Triage RN then performs on the Mr. Public the:
   1. National Institutes of Health Stroke Scale (NIHSS) Assessment
   2. Rapid Arterial Occlusion Evaluation (RACE)
   3. Following completion of these two tests, the RN is able to compare results to those obtained from the individual at baseline.
G. Brain Attack Triage Discussion/Confirmation
   Based on the preliminary FAST answers provided via the BATE, and the Triage RN's assessment of the subject via determination of the NIHSS and RACE scores, an initial decision is made by the RN to:
   1. Scenario 1. Reassure Mr. Public (and others involved) that this does not appear to be a brain attack.
   2. Scenario 2. Consult with on-call Stroke (Brain Attack) Neurologist regarding diagnosis, and need for follow-up care.
      a. Follow-up with PCP or Specialist
      b. Follow-up with Neurologist
   3. Scenario 3. Consider activating the EMS system for emergent transport to hospital for assessment and treatment
      a. A rapid consultation with on-call MD (Stroke Neurologist) regarding clinical status, test results, and other data supporting emergent transport and treatment.
      b. Define the optimal treatment site based on condition, and likelihood of LVO, based on RACE, or other diagnosis requiring rapid treatment.
      c. Triage RN and MD activate optimal routing program for EMS to specific treatment center.
      d. Triage MD communicates directly with a) EMS and b) selected treatment center, updating EMS regarding individual's current status and likely condition, prescribing initial EMS diagnostics, monitoring, and treatments, and providing impression and recommendations to ER physician at treatment center, in addition to initiating communication between EMS and treatment hospital.

In one embodiment, the invention features a system for tracking the health of an individual relative to health norms and deviations relevant to that individual and proposing effective interventions in the event of such deviations. The system includes a first biosensor or set of biosensors configured to acquire a physiological signal from an individual; a first element configured to acquire health data of the individual from one or more data streams; a second element adapted to receive and integrate the physiological signal from the individual and the health data of the individual, wherein the element is configured to predict and/or recognize brain attack in the individual based on an integration of the physiological signal from the individual and the health data of the individual; a third element configured to activate if such identification occurs and alert a first provider via such activation of a possible interruptive health event; a fourth element configured to interact with the individual in real-time and enable the first provider to propose to the individual and/or a caregiver and/or a second provider one or more effective interventions; and a fifth element configured to initiate and interact with the individual and/or first and/or second provider in real-time and determine that effective interventions were made.

Implementations of an embodiment of the invention may include one or more of the following features. The brain attack tracked may be an ischemic stroke, a hemorrhagic stroke, an intracerebral hemorrhage, a subarachnoid hemorrhage, a seizure, or a secondary ischemic stroke.

The third element may comprise an application for a mobile or cellular device that can communicate with the first provider.

The fourth element may comprise an audio or video interface for communication with the individual to conduct an automated stroke triage procedure. The fourth element may further comprise an audio or video interface for communication with the individual, the first provider, and the second provider to conduct an automated brain attack triage procedure or an augmented brain attack triage procedure mediated by the first provider and/or the second provider.

The fifth element may comprise a text, call, email, audio, or video interference for communication with the individual and/or first provider and/or second provider.

In another embodiment, the third and fourth elements may be the same.

In another embodiment, the fifth element may be absent.

In other embodiments of the invention, the biosensor or set of biosensors may include a body-mass-index (BMI) monitor, a physiological stress monitor, a heart monitor, a blood pressure monitor, an oxygen level monitor, a vital sign monitor or combinations thereof. The biosensor or set of biosensors may be worn by the individual.

In an embodiment of the invention, the first element may be configured to collect supporting data. These supporting data may comprise family health data of family members of the individual, dietary habits data of the individual, behavioral aspects data of the individual or general population norms data. The first element may include a non-biosensor. The non-biosensor may be configured to collect a non-physiological signal from, e.g., an accelerometer activity, an acoustic activity, an ambient lighting condition and/or a global positioning system. The biosensor or set of biosensors and the non-biosensor may collect data continuously and unobtrusively. The biosensor or set of biosensors may collect data continuously and unobtrusively and the non-biosensor may collect data periodically or intermittently.

In an embodiment of the invention, the second element may be configured such that integration of the physiological signal is continuous and real-time. This second element may include an inference engine. The inference engine may integrate the physiological signal from the individual, the health data of the individual and the supporting data to predict and/or recognize secondary ischemic stroke in the individual. The inference engine may execute this prediction and/or recognition by assessing impending deviations from the individual's normal health trajectories.

In one embodiment, the invention features a method for tracking the health of an individual relative to health norms and deviations relevant to that individual. This tracking method includes collecting one or more physiological signals from the individual using a biosensor or set of biosensors. The method also comprises collecting health data of the individual from one or more data streams using a first element. The method further comprises receiving and integrating the physiological signal from the individual and the health data of the individual using a second element, such as an inference engine. The method includes predicting and/or recognizing brain attack in the individual based on an integration of the physiological signal from the individual and the health data of the individual using the second element. The method further includes activating an alert to and/or communication with a first provider of a possible interruptive health event of the individual using a third element. The method further includes communicating using a fourth element by the first provider with the individual in real-time to propose to the individual and/or a caregiver and/or a second provider one or more effective interventions. The method further includes initiating and interacting with the individual and/or first and/or second provider in real-time and determine that effective interventions were made using a fifth element.

Implementations of an embodiment of the invention may include one or more of the following features. The brain attack tracked may be an ischemic stroke, a hemorrhagic stroke, an intracerebral hemorrhage, a subarachnoid hemorrhage, a seizure, or a secondary ischemic stroke.

The third element may comprise an application for a mobile or cellular device that can communicate with the first provider.

The fourth element may comprise an audio or video interface for communication with the individual to conduct an automated brain attack triage procedure. The fourth element may further comprise an audio or video interface for communication with the individual, the first provider, and the second provider to conduct an automated brain attack triage procedure or an augmented brain attack triage procedure mediated by the first provider and/or the second provider.

The fifth element may comprise a text, call, email, audio, or video interference for communication with the individual and/or first provider and/or second provider.

In another embodiment, the third and fourth elements may be the same.

In another embodiment, the fifth element may be absent.

In other embodiments of the invention, the method may utilize a biosensor or set of biosensors, which may include a body-mass-index (BMI) monitor, a physiological stress monitor, a heart monitor, a blood pressure monitor, an oxygen level monitor, a vital signs monitor or combinations thereof. The biosensor or set of biosensors may be worn by the individual.

In an embodiment of the invention, supporting data may be collected using a first element. These supporting data may comprise family health data of family members of the individual, dietary habits data of the individual, behavioral aspects data of the individual or general population norms data. The first element may include a non-biosensor. The non-biosensor may be configured to collect a non-physiological signal from, e.g., an accelerometer activity, an acoustic activity, an ambient lighting condition and/or a global positioning system. Data may be collected continuously and unobtrusively using the biosensor or set of biosensors and the non-biosensor. The biosensor or set of biosensors may collect data continuously and unobtrusively and the non-biosensor may collect data periodically or intermittently.

In an embodiment of the invention, the integration of the physiological signal by the second element may be continuous and real-time. This second element may include an inference engine. Integration of the physiological signal from the individual, the health data of the individual and the supporting data to predict and/or recognize brain attack in the individual may be accomplished by the second element, e.g., an inference engine. This prediction and/or recognition may be accomplished by the second element by assessing impending deviations from the individual's normal health trajectories.

In another embodiment of the invention, the fused data are captured by biosensors and other elements from real-time telemetry of vital signs, accelerometer activity, acoustic activity, ambient lighting, location via global positioning system (GPS), etc. and are integrated by an element such as an inference engine with information from real-time Internet sources to infer and create personalized health care indicators. The inference engine gradually "learns" an individual's regular level and timing of activity measures, and "infers" if the current health state of the individual varies from their historical normal health state, the established health norms for that specific individual. An individual's overall state of health refers to the combination of the state of mind (psychological), comprising, but not limited to, memory, orientation, insight, judgment, abstract thinking, behavior, sensorium, as well as a self-perceived ability to perform tasks, and the general physical state (physiological) of being. Defining the state of health must be done at the proper granularity to enable what is known in the art as seasonal analysis. For example, many people are less active in winter than summer due to the temperature and period of daylight available. Likewise, people are less physically and mentally active during their periods of sleep (normally at night) than during their waking (typically daylight except for phase-shifted workers) hours. Such activity patterns may be automatically and passively detectable in individuals, without direct patient involvement, as well as variations from the individual's established normal state.

Traditionally, the focus of intervention is on detecting anomalies from a time series of telemetry data points. However, all that tells us is that something happened at a particular time. In other words, something happened at a certain time for a given duration. In contrast, an embodiment of the invention uses biosensors and other elements to process events and apply event mining for determining specific causality for a specific person, and forming their objective personal model based on passively collected data. Simply put, an embodiment of the invention raises the state of the art from processing data to get a time-based analysis of signals to an event-based analysis of continuously gathered information by biosensors and other elements to an actionable knowledge-based intervention.

Specifically, an embodiment of the invention improves individual health and promotes wellness by using biosensors and other elements to (1) collect various wearable biosensor and other data, continuously and unobtrusively; (2) integrate available patient specific data points and known general population norms for medical data; (3) mine events in the collected data streams to build an objective personal model of the individual; and (4) assess individual personal health trends, inform the individual (and providers as previously defined) of impending deviations from individuals' normal health trajectories, and (5) via the intervention of one or more providers suggest and effect methods to mitigate or prevent significant deviations from health and towards known disease characteristics.

An embodiment of the invention accomplishes the following by designing, verifying, analyzing, implementing and evaluating algorithms that: (1) capture diverse signals and store them in an appropriate form that supports data integration from across biosensors and other elements; (2) determine personal daily activities of individuals and relating those to other events for building objective personal models; (3) identify potential physiological and/or psychological conditions in an individual prior to onset of clinical symptoms. In doing so, an embodiment of the invention enables the personalization of treatment, namely, supporting personalized medicine. Also using the personal model, the system predicts and recommends appropriate actions before a serious event may occur.

One embodiment of the invention focuses on the prevention of secondary ischemic stroke. Signs of ischemic stroke include, but are not limited to, sudden:
- Facial or limb weakness or numbness particularly affecting one side of the body;
- Loss of balance or coordination
- Difficulty speaking or seeing;
- Confusion;
- Severe headaches Any or all combinations of these as well as additional signs are detectable using biosensors and other elements of various types and can be fused using an element such as an inference engine, providing a diagnosis, which can automatically issue an urgent alert for intervention to the individual and their healthcare team, and are within an embodiment of the invention.

Specifically, an embodiment for ischemic stroke detection tracks and monitors the following symptoms using the following example devices including the following example biosensors and elements. Note that one skilled in the art understands that additional clinical conditions beside ischemic stroke can also be tracked and monitored, and other specific tracking capabilities might be required; however, such practice still is covered by an embodiment of the invention as the embodiment disclosed is merely used as exemplary.

- Heart related activity—captured either via a wearable biosensor or via a specific element attached to a smartphone (as known in the art)
  - Heart rate (HR) monitor: Baseline, accelerations, decelerations, and fast Fourier transform (FFT) for "power spectra"
  - Heart rhythm determination:
    - Normal sinus—Total fraction of time during daily monitoring;
    - Presence and type of ectopic ventricular beats [known in the art as singlets, doublets, triplets, and/or short runs]; or ventricular tachycardia;
    - Presence and type of atrial arrhythmias [known in the art as atrial fibrillation (irregularly irregular), atrial flutter, and/or other supraventricular tachyarrhythmias].
- General activity indicators—accelerometer or element attached to smartphone or smartphone applications (as known in the art)
  - Fraction of day spent exercising, with a maximum heart rate (MHR); age-adjusted MHR=220-age;
  - Time of day spent supine, standing, moving or sitting;
  - Ability to sleep flat or need to have head inclined;
  - Steps/Miles walked/Stairs climbed per day;
  - Sleep quantity and quality, as known in the art
- Blood pressure—captured via element attached to smartphone (as known in the art)
  - Diastolic and systolic at rest and supine, compared to when standing, walking, or jogging.
- Respiratory status—captured via element attached to smartphone (as known in the art)
  - Oxygen saturation (venous/arterial) at rest compared to during movement/exercise
- Serial Multi-omic analyses of blood components (as known in the art)—Including, but not limited to:
  - From white blood cells (WBC or leukocytes)—deoxyribonucleic acid (DNA) extraction provides a substrate for genomics and epigenomics analyses; ribonucleic acid (RNA) extraction provides substrate for transcriptomics analyses, for example:
    - Gene mutations associated with pro-coagulopathies;
    - Specific histone modifications or promoter methylation status associated with pro-coagulopathies;
    - Transcripts defined via variant analyses that are linked with pro-coagulopathies;
  - From plasma—analytic results related to Exosomics, Proteomics, and Metabolomics; for example:
    - Altered exosomal cargo molecules associated with pro-coagulopathies;
    - Altered plasma protein levels associated with pro-coagulopathies;
    - Altered metabolites associated with pro-coagulopathies;
- Structured and textual extraction (as known in the art) from available Electronic Health Records (mandated as part of the Affordable Care Act)
  - History of type 2 diabetes—degree of control via fasting glucose measure; Hemoglobin A1c levels;
  - History of pro-coagulopathy;
  - History of deep vein thrombosis (DVT) and/or pulmonary embolism (PE);
  - History of heart failure (HF);
  - Ejection fraction (EF) measure;
  - History of ventricular aneurysm;
  - History of enlarged left atrium (>4 cm), valvular disease (tricuspid stenosis, tricuspid regurgitation, pulmonary (bicuspid) stenosis, pulmonary (bicuspid) regurgitation, mitral stenosis, mitral regurgitation, aortic stenosis or aortic regurgitation);
  - History of extracranial atherosclerotic carotid or aortic arch disease;
  - History of intracranial arterial stenoses, occlusions, ectasias, or other abnormalities;
  - History of fibromuscular dysplasia (FMD);
  - Medications—historical; current
  - D-dimer levels in blood
- Extractions from verified published sources or validated Internet (as known in the art)
  - Population health statistics and diversity of norms
- Conventional diverse readings by biosensors and/or other elements—maintained over a prolonged period, measuring and noting specific deviations in readings from personal norms; attachments to or components of smartphone technology (as known in the art)
  - Weight fluctuations
  - Respiratory rate
- Dietary and ingestion indicators via smartphone applications (as known in the art)
  - Salt intake;
  - Fluid intake; quantity and quality (type of fluid);
  - Urine output
  - Diet: Calories, type (carbs, fats [sat/unsat], fructose, protein, etc.);
  - Timing of caloric intake during day (or night); frequency of caloric intake;
  - Medications taken in reference to meals, fluids;

Vitamin supplements taken in reference to meals, fluids;

Additionally, in an embodiment of this invention, non-conventional elements are used to capture and augment telemetry and are incorporated by the inference engine to support prescriptive intervention. As non-limiting examples are two common modes of transportation and how they may be used to inform about individual health status—driving and flying. In both cases, telemetry obtained as part of those activities can be used to augment an individual's health profile. The transfer of such telemetry data to the inference engine might be accomplished via the user's smartphone by an established agreement between the individual and those charged with capturing the data in those specific modes of transportation.

- Drivers of automobiles continuously experience stress; this is particularly the case in congested metropolitan traffic, and even more so, during the morning and evening rush hours. If an instrumented motor vehicle allows the capture and transmission of health-related data points (e.g., heart rate and rhythm, hand perspiration, respiration rate, body temperature, body weight, etc.), possibly via the steering wheel or other built in biosensors, or via the automobile's seat (i.e., to determine weight), an individual's health condition can be continuously monitored, including their reactions to stress. The latter could be correlated to known traffic conditions, weather, etc. as determined via navigation, weather, and other information available via applications on or attachments to smartphones.
- As another example, individuals traveling into an airport could have their body mass index (BMI) serially determined through the use of 3D imaging technologies, as utilized by TSA for screening and security clearance. The TSA scanning equipment could produce additional informative medical information about an individual, including, but not limited to, the relative position and time-dependent accumulation of adipose tissue in the body, some of which has been clearly associated with increased medical risk.

In short, many additional readings from daily activities can easily be collected by biosensors and other elements and processed for guidance via an individual's inference engine. Fundamentally, therefore, an embodiment of the invention relies on a diversity of data collected continuously, either passively (without any user awareness), with user interaction but non-invasively (e.g., answering periodic questions or taking pictures), via daily activities obtained from non-health focus devices (e.g., cars, TSA, etc.), patient health records or diagnostic tests, population data and norms, and environmental data (traffic, air pollution, weather, etc.) and norms. All these data points are cleaned, fused, interpolated, and processed by any relevant statistical means, and are ingested by an embodiment of the invention's inference engine. Once the individual's typical state of health is learned (iteratively and adaptively over time) via the various data point inputs, significant deviations from the individual's expected state over time (trajectory) are detected, noted for further analysis, with causality determined or inferred, as possible, and corrective measures prescribed. Results of the corrective intervention are monitored, learned, and incorporated into the knowledge base of the personal model, while feedback is provided to the individual and their healthcare team, with follow-up recommendations for monitoring and other prescriptions.

An embodiment of the invention capitalizes on multiple differentiating practices:

- Much of the monitoring is continuous—unlike conventional efforts that rely on periodic telemetry, wear-able and carry-able sensor technologies are able to continuously collect readings
- Personalized focus—the inference engine creates an individual model; including the generalities and norms provided by populations
- A diversity of sensors are used—these sensors include non-health targeted readings collected from daily activity and evolving environmental monitoring
- Interventions are prescribed through the intervention of one or more providers and their impact is assessed in real time Overall, an embodiment of the invention provides actionable, prescriptive and/or proscriptive (don't consume too much salt) information to individuals that can direct toward or preserve a healthy lifestyle and help sustain the quality of life and well-being.

An addition embodiment of the invention relates to establishing keys to a predictive platform for ischemic stroke.

The current ischemic stroke prevention guidelines encourage evaluation and management via risk mitigation within as soon as possible following either a transient ischemic attack (TIA) or ischemic stroke, and certainly within the first 2 weeks.

The term "TIA" is defined classically as a brief episode of neurological dysfunction caused by a focal disturbance of brain or retinal ischemia lasting less than 24 hours and without evidence of infarction (Albers G W, Caplan L R, Easton J D, et al; TIA Working Group. Transient ischemic attack: proposal for a new definition. *N Engl J Med* 2002; 347(21): 1713-1716).

According to Wu, C M, et al, *Arch Intern Med* 2007; 167(22): 2417-2422, the greatest risk of ischemic stroke following a TIA occurs within the first week as shown in Table 4.

TABLE 4

The risk of stroke following a TIA

| Risk at | 2 Days | 30 Days | 90 Days |
|---|---|---|---|
| Across studies surveyed: | 1.4%-9.9% | 3.2%-17.7% | 3.9%-17.3% |
| Using a random effects model (95% CI): | 3.5% (2.1%-5.0%) | 8.0% (5.7%-10.2%) | 9.2% (6.8%-11.5%) |
| Passive Ascertainment (Determined via assessment of administrative data) | 3.1% | 6.4% | 8.7% |
| **Active Ascertainment (Determined via direct clinical assessment) | 9.9% | 13.4% | 17.3% |

What specific risk factors modulate ischemic stroke risk following TIA? The effects associated with ABCD2 score are shown in Table 5.

TABLE 5

Risk for Stroke at Various Time Points After TIA Based on $ABCD^2$ Score*

| | |
|---|---|
| Age: | ≥60 years = 1 point |
| Blood pressure: | Systolic blood pressure ≥140 mmHg and/or diastolic blood pressure ≥90 mmHg = 1 point |
| Clinical features: | Unilateral weakness = 2 points |
| | Speech disturbance without weakness = 1 point |
| Duration of symptoms: | ≥60 minutes = 2 points |
| | 10-59 minutes = 1 point |
| Diabetes: | Yes = 1 point |

TABLE 5-continued

Risk for Stroke at Various Time Points After TIA Based on ABCD² Score*

| ABCD² Score | Risk Category | Stroke Risk | | |
|---|---|---|---|---|
| | | 2 Days | 7 Days | 90 Days |
| 0-3 | Low | 1.0 | 1.2 | 3.1 |
| 4-5 | Moderate | 4.1 | 5.9 | 9.8 |
| 6-7 | High | 8.1 | 11.7 | 17.8 |

*Modified from Cuccchiara and Kasner, Ann Int Med 2011, 154(1): ITC1-1. doi: 10.7326/0003-4819-154-1-201101040-01001

What is an ischemic stroke? It is the sudden death of brain cells due to lack of oxygen, caused by insufficient blood flow to a portion of the brain. Sudden loss of speech, weakness, or paralysis of one side of the body are common clinical signs. These manifestations typically last for >24 hours and may cause permanent neurological sequelae. Neuroimaging with CT or MRI ultimately show signs of infarction.

What factors determine the impact of an ischemic stroke? The size and location of the stroke are the primary determinants of impact on the individual.

Figure 10:
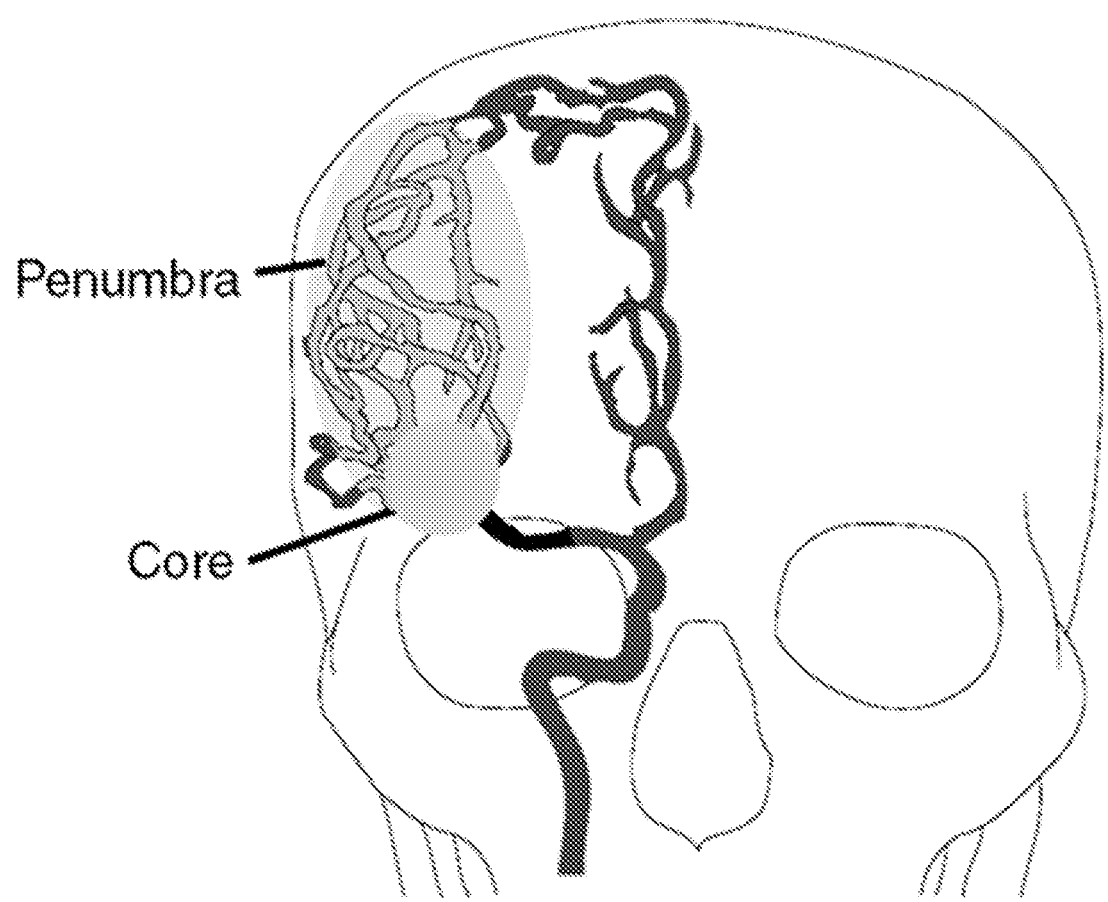
FIG. 10 shows a schematic of the interior of a human brain, with a large vessel occlusion, small region of ischemic stroke (with irreversible cell injury), and ischemic region surrounding the stroke (potentially reversible region).

The Core (see FIG. 10) of a stroke is the area of parenchymal cell death, typically associated with local cerebral blood flow (CBF) of <10 ml/100 gms tissue/min, just distal to a vessel blockage or occlusion (see black segment of blood vessel just below Core) caused by a blood clot (thrombus or embolus) or a significant narrowing or stenosis.

The ischemic Penumbra (see FIG. 10) of an ischemic stroke is the "at risk" area of brain parenchyma that is typically surrounding the Core, which is not functioning normally, with CBF ranging from 10-35 ml/100 gms tissue/min. This ischemic penumbra may ultimately progress to extend the core, via progressive infarction, or return to more normal function, based primarily on how long the limitation in blood flow (and oxygen) is maintained. The size of the ischemic penumbra in individuals with similar vessel occlusions is variable and dependent upon the collateral circulation as well as the location of the Core.

What is the risk of a recurrent stroke following an initial stroke? The pooled cumulative risk was 3.1% (95% CI, 1.7-4.4) at 30 days, 11.1% (95% CI, 9.0-13.3) at 1 year, 26.4% (95% CI, 20.1-32.8) at 5 years, and 39.2% (95% CI, 27.2-51.2) at 10 years after initial stroke (Mohan K M, et al, Stroke. 2011; 42:1489-1494.)

Based on these studies, we can begin to consider the following Observables and Inputs to the Risk Determination/Mitigation Platform:

Observables (see Table 6):

Age≥60 years

Systolic BP≥140 mm Hg and/or Diastolic BP≥90 mm Hg

Unilateral weakness

Unilateral numbness

Speech abnormality without weakness or numbness

Transient, painless loss of vision (amaurosis fugax)

Clinical symptoms lasting >60 minutes

Clinical symptoms lasting 10-59 minutes

Known history of diabetes mellitus

Body mass index>30

EKG

Stress Test (Treadmill, Persantine thalium)

Transesophageal Echocardiogram (TEE)

D-dimer levels (plasma) (Barber M, et al, Stroke. 2006; 37:1113-1115; and Zhang J, et al, Oncotarget, 2018, Vol. 9, (No. 2), pp: 2208-2219)

Bleeding risk

History of deep vein thrombosis (DVT)

History of Atrial Fibrillation (Afib)

Hereditary coagulopathy

History of smoking

History of alcohol or drug abuse

Sedentary lifestyle (From Friedman T, et al, Plast. Reconstr. Surg. 125: 1544, 2010.)

TABLE 6

National Institute of Health Stroke Scale

| Tested Item | Title | Responses and Scores |
|---|---|---|
| 1A | Level of Consciousness | 0 - Alert<br>1 - Drowsy<br>2 - Obtunded<br>3 - Coma / Unresponsive |
| 1B | Orientation Questions (2) | 0 - Answers both questions correctly<br>1 - Answers 1 correctly<br>2 - Answers neither correctly |
| 1C | Response to Commands (2) | 0 - Performs both tasks correctly<br>1 - Preforms 1 task correctly<br>2 - Performs neither |
| 2 | Gaze | 0 - Normal horizontal movements<br>1 - Partial gaze palsy<br>2 - Complete gaze palsy |
| 3 | Visual Fields | 0 - No visual field defect<br>1 - Partial hemianopia<br>2 - Complete hemianopia<br>3 - Bilateral hemianopia |
| 4 | Facial Movement | 0 - Normal<br>1 - Minor facial weakness<br>2 - Partial facial weakness<br>3 - Complete unilateral palsy |
| 5 | Motor Function (arm)<br>a. Left<br>b. Right | 0 - No drift<br>1 - Drift before 10 s<br>2 - Falls before 10 s<br>3 - No effort against gravity<br>4 - No movement |
| 6 | Motor Function (leg)<br>a. Left<br>b. Right | 0 - No drift<br>1 - Drift before 5 s<br>2 - Falls before 5 s<br>3 - No effort against gravity<br>4 - No movement |
| 7 | Limb ataxia | 0 - No ataxia<br>1 - Ataxia in 1 limb<br>2 - Ataxia in 2 limbs |
| 8 | Sensory | 0 - No sensory loss<br>1 - Mild sensory loss<br>2 - Severe sensory loss |
| 9 | Language | 0 - Normal<br>1 - Mild aphasia<br>2 - Severe aphasia<br>3 - Mute of global aphasia |
| 10 | Articulation | 0 - Normal<br>1 - Mild dysarthria<br>2 - Severe dysarthria |
| 11 | Extinction or inattention | 0 - Absent<br>1 - Mild loss (1 sensory modality lost)<br>2 - Severe loss (2 modalities lost) |

Adapted from Lyden et al Copyright© 1994, American Heart Association, Inc. Other factors include hereditary disorder and high stress environment (see Table 7).

TABLE 7

Major hereditary thrombophilia disorders, risk level, and commonly recommended venous thromboembolism prophylaxis

| Condition | Risk for VTE | Generally Recommended Prophylaxis* |
|---|---|---|
| Genetic mutations of coagulation factors | | |
| Activated protein C factor V Leiden | Mild | Mechanical device (e.g., SCDs) and perioperative chemoprophylaxis; consideration may be given to continuing pharmacologic agents for up to 28 days after discharge[18] |
| Prothrombin G20210A | Mild | |
| Elevated levels of factors VIII, IX, and XI | Mild | |
| Deficiency of anticoagulant protein | | |
| Protein S deficiency | Moderate | |
| Protein C deficiency | Moderate to severe | |
| Antithrombin deficiency | Severe | |

VTE, venous thromboembolism;
SCDs, serial compression devices.
*Only applicable to patients who are not already on prolonged anticoagulation therapy before surgery. Exact regimens for specific cases may vary based on a detailed evaluation and risk assessment by a hematologist.

Family history of Stroke
Carotid artery atherosclerotic disease
Aortic/brachiocephalic atherosclerotic disease
Aortic/mitral valvular disease
Fibromuscular dysplasia (FMD)
Hyperlipidemia
History of myocardial infarction
Cardiac aneurysm
Left atrial enlargement (LAE)
Sleep disordered breathing
Postmenopausal hormone replacement therapy
Polycythemia or thrombocytopenia The frequency of hereditary thrombophilia is shown in Table 8.

TABLE 8

Frequency of hereditary thrombophilia

| Thrombophilia | General Population (heterozygous frequency)[11,15-17] | Individuals with a VTE Who Test Positive[11,15-17] |
|---|---|---|
| Factor V Leiden | 1 in 20 | 1-2 in 10 |
| Prothrombin gene variant | 2-3 in 100 | 5-10 in 100 |
| Antithrombin deficiency | 1 in 500 | 1 in 25 |
| Protein C deficiency | 1 in 500 | 1 in 50 |
| Protein S deficiency | 3-13 in 1000 | 1 in 50 |

VTE, venous thromboembolism.

Table 9 includes six simple questions to ask every patient at risk of stroke.

TABLE 9

Six simple questions to ask every patient
Sample Questionnaire for Patients

| | | |
|---|---|---|
| Have you or anyone in your family ever had a blood clot? | Yes | No |
| Have you or anyone in your family ever been on blood thinners? | Yes | No |
| Have you or anyone in your family ever been diagnosed with a blood clotting disorder? | Yes | No |
| Has anyone in your family had a disease called "purpura fulminans?" | Yes | No |
| Have you ever been diagnosed with lupus or any other autoimmune disease? | Yes | No |
| For female patients: have you ever had a miscarriage? | Yes | No |

Protein C activity
Protein S activity
Antiphospholipid antibody testing (lupus anticoagulant, anticardiolipin, anti-beta2-glycoprotein I)
Inputs
Antiplatelet therapy (ASA, other)
Anticoagulation therapy (Warfarin, oral anticoagulants)
Statin therapy
Other antilipidemic agents
Mechanical Thrombectomy
Thrombolytic therapy (Alteplase; TPA)
CT Angiogram
CT Perfusion scan
structural MRI; diffusion weighted MRI
DVT prophylaxis (pneumatic compression, Aspirin)
Mild to Moderate Exercise
Low fat, low carbohydrate diet
Closure of patent foramen ovale (PFO)
Stress reduction (Yoga, meditation)
Smoking cessation
Reduction or elimination of alcohol or drugs
Improved control of blood glucose; reduction of Hgb A1c (to <5.7%)
Weight reduction We have described a new approach to health-tracking of individuals using biosensors and other elements to collect and integrate health data from one or more data streams. This approach allows the benefits of predicting and/or recognizing health deviations likely resulting in interruptive health events and proposing one or more effective interventions to prevent the onset of such interruptive health events. One feature of the described method is that it changes healthcare orientation by directing attention to individuals and their respective personalized norms and not population health standards defined epidemiologically.

Although the results have been illustrated using a health tracking system configuration based on biosensors and other elements to monitor interruptive health events, such as brain attack, the basic concept is equally applicable with another other type of deviation from an individual's normal health trajectory.

Other embodiments are also within the scope of the following claims.

What is claimed is:

1. A brain attack triage system (BATS) comprising:
   a biosensor or plurality of biosensors configured to acquire a physiological signal from an individual;
   a first element configured to acquire health data of the individual from one or more data streams;
   a second element adapted to receive and integrate the physiological signal from the individual and the health data of the individual, wherein the second element is configured to predict and/or recognize a brain attack in the individual based on an integration of the physiological signal from the individual and the health data of the individual;
   a third element configured to activate if the second element recognizes the brain attack in the individual and alert a first provider via such activation of a possible interruptive health event;
   a fourth element configured to interact with the individual in real-time and enable the first provider to propose to the individual and/or a caregiver and/or a second provider one or more effective interventions; and
   a fifth element configured to initiate and interact with the individual and/or the first and/or the second provider in real-time and determine that effective interventions were made;
   wherein the system provides real-time feedback of the individual to a family member of the individual, and validates the activation of the system.

2. The system of claim 1, wherein the third and fourth element are integrated in a same device.

3. The system of claim 1, wherein the plurality of biosensors includes a body-mass-index (BMI) monitor, a physiological stress monitor, a heart monitor, a blood pressure monitor, an oxygen level monitor, a vital signs monitor, or combinations thereof.

4. The system of claim 3, wherein the plurality of biosensors is worn by the individual.

5. The system of claim 1, wherein the brain attack is one of an ischemic stroke, a hemorrhagic stroke, an intracerebral hemorrhage, a subarachnoid hemorrhage, a seizure, or a secondary ischemic stroke.

6. The system of claim 1, wherein the first element is configured to acquire supporting data comprising family health data of family members of the individual, dietary habits data of the individual, behavioral aspects data of the individual or general population norms data.

7. The system of claim 6, wherein the first element includes a non-biosensor.

8. The system of claim 7, wherein the non-biosensor is configured to acquire a non-physiological signal from an accelerometer activity, an acoustic activity, facial recognition, an ambient lighting condition and/or a global positioning system.

9. The system of claim 7, wherein the non-biosensor and the biosensor or the plurality of biosensors collect data continuously and unobtrusively.

10. The system of claim 7, wherein the biosensor or the plurality of biosensors collect data continuously and unobtrusively and the non-biosensor collect data periodically or intermittently.

11. The system of claim 1, wherein relevant information regarding activation of the system is shared with the individual and the caregiver.

12. The system of claim 1, wherein the second element comprises a brain attack triage engine (BATE) including an inference engine.

13. The system of claim 12, wherein the inference engine integrates the physiological signal from the individual and the health data of the individual to identify a feature associated with the brain attack in the individual by assessing a deviation from a normal health trajectory of the individual, indicating a possible interruptive health event and activating the third element if said deviation is detected with the purpose of mitigating or preventing significant deviations from the individual's health and toward known disease characteristics.

14. The system of claim 12, wherein the inference engine integrates the data by maintaining data security and personal privacy of the individual using encryption.

15. The system of claim 12, wherein the inference engine integrates the data by utilizing multiple individual data sets to provide improved understanding of a population, allowing for identification of parameters that define a range of individual norms and deviation from said individual norms.

16. The system of claim 15 wherein the inference engine integrates data related to illnesses, medications, and behaviors for a population by combining data points from individuals of the population.

17. The system of claim 12, wherein the inference engine continuously monitors a success of prescribed interventions and if the prescribed interventions are unsuccessful, alternate solutions are provided, wherein the individual and a predetermined healthcare response team are notified of the prescribed interventions and their apparent affects.

18. The system of claim 12, wherein the inference engine integrates genomic data of the individual from one or more data streams.

19. The system of claim 18, wherein the genomic data includes Serial Multi-omic analyses of blood components.

20. The system of claim 19, wherein the Serial Multi-omic analyses of blood components comprises deoxyribonucleic acid (DNA) extraction, wherein the DNA provides a substrate for genomic analysis.

21. A method of integration of data in real-time by a hospital using the system of claim 1, the method comprising:
   activation of the system by the individual or the caregiver based on perceived abnormalities provided by the biosensor or the plurality of biosensors compared to baseline values;
   alerting a triage nurse wherein the triage nurse rapidly reviews past clinical information of the individual, wherein the individual is assessed and recorded by an artificial intelligence-driven (AI-driven) question and answer (Q & A) session, wherein the triage nurse immediately reviews baseline audio and video exams of the individual prior to direct interaction, wherein following the AI-driven Q & A session, the triage nurse directly assesses the individual via video/audio interview;
   rapid assessment of available information by the triage nurse and a triage physician to confirm the brain attack using AI-driven Q & A results, and the audio/video interview in comparison of the baseline audio and video exams; and
   initiating supplementary communication between the individual or caregiver, emergency personnel, and the triage nurse or physician until the individual's transport is completed and arrival to the hospital for definitive assessment and treatment, wherein digital alerts are sent to other healthcare providers of the individual, with a summary of assessments, a triage decision, and a location of treatment site.

22. A method of integration of data in real-time by a hospital using the system of claim 1, the method comprising:

activation of communication and assessment by an inference engine based on perceived abnormalities provided by the biosensor or the plurality of biosensors compared to baseline values;

alerting a triage nurse wherein the triage nurse rapidly reviews past clinical information of the individual, wherein the individual is assessed and recorded by an artificial intelligence-driven (AI-driven) question and answer (Q & A) session, wherein the triage nurse reviews baseline audio and video exams of the individual prior to direct interaction, wherein following the AI-driven Q & A session, the triage nurse directly assesses the individual via video/audio interview;

rapid assessment of available information by the triage nurse and a triage physician to confirm the brain attack using the AI-driven Q & A results, and the audio/video interview in comparison of the baseline audio and video exams of the individual; and initiating supplementary communication between the individual or caregiver, emergency personnel, and the triage nurse or physician until the individual's transport is completed and arrival to the hospital for definitive assessment and treatment, wherein digital alerts are sent to other healthcare providers of the individual, with a summary of assessments, a triage decision, and a location of treatment site.

\* \* \* \* \*